(12) United States Patent
Rohr et al.

(10) Patent No.: US 7,423,008 B2
(45) Date of Patent: Sep. 9, 2008

(54) DERIVATIVES OF MITHRAMYCIN AND METHODS OF MAKING AND USES THEREOF

(75) Inventors: Jurgen Rohr, Georgetown, KY (US); Lily L. Remsing, Lexington, KY (US); Mohammad Nur-e-Alam, Lexington, KY (US); Jose A. Salas, Oveledo (ES); Carmen Mendez, Oviedo (ES); Alfredo F. Braña, Gijon (ES); Ana M. Gonzàlez, Palencia (ES)

(73) Assignees: University of Kentucky Research Foundation, Lexington, KY (US); Universidad de Oviedo, Ovideo (FR)

( * ) Notice: Subject to any disclaimer, the term of this patent is extended or adjusted under 35 U.S.C. 154(b) by 485 days.

(21) Appl. No.: 10/796,304

(22) Filed: Mar. 10, 2004

(65) Prior Publication Data

US 2005/0192432 A1 Sep. 1, 2005

Related U.S. Application Data

(60) Provisional application No. 60/548,175, filed on Mar. 1, 2004.

(51) Int. Cl.
*A01N 61/00* (2006.01)
*A01N 63/00* (2006.01)
*C12P 1/00* (2006.01)
*A61K 39/00* (2006.01)
*A61K 45/00* (2006.01)

(52) U.S. Cl. .................... 514/1; 435/41; 424/93.43; 424/278.1; 424/282.1

(58) Field of Classification Search .............. 424/278.1, 424/282.1, 93.43; 435/41; 514/1
See application file for complete search history.

(56) References Cited

U.S. PATENT DOCUMENTS

| | | |
|---|---|---|
| 3,592,925 A | 7/1971 | Evans, Jr. et al. |
| 3,646,194 A | 2/1972 | Sobin et al. |
| 3,821,085 A | 6/1974 | Zhdanovich et al. |
| 3,906,093 A | 9/1975 | Sobin et al. |
| 4,141,974 A | 2/1979 | Davies et al. |
| 4,452,786 A | 6/1984 | Mitsuhashi et al. |
| 4,511,560 A | 4/1985 | Tomita et al. |
| 4,935,445 A | 6/1990 | Merry |
| 5,057,304 A | 10/1991 | Kretzschmar et al. |
| 5,656,736 A | 8/1997 | Nakano et al. |
| 5,723,448 A | 3/1998 | Gross et al. |

OTHER PUBLICATIONS

Lily L. Remsing, et al. "Mithramycin SK, A Novel Antitumor Drug with Improved Therapeutic Index, Mithramycin SA, and Demycarosyl-mithramycin SK: Three New Products Generated in the Mithramycin Producer *Streptomyces argillaceus* through Combinatorial Biosynthesis" J. Am. Chem. Soc. 2003, 125, pp. 5745-5753.

Robert J. Ferrante, et al. "Chemotherapy for the Brain: Mithramycin Prolongs Survival in a Model of Huntington's Disease".

L. Prado, et al. "Analysis of two chromosomal regions adjacent to genes for a type II polyketide synthase involved in the biosynthesis of the antitumor polyketide mithramycin in *Streptomyces argillaceus*." 1: Mol Gen Genet. Mar. 1999;261(2):216-25.

G. Blanco, et al. "Characterization of two glycosyltransferases involved in early glycosylation steps during biosynthesis of the antitumor polyketide mithramycin by *Streptomyces argillaceus*." 1: Mol Gen Genet. Jan. 2000;262(6):991-1000.

MJ Lozano, et al. "Characterization of two polyketide methyltransferases involved in the biosynthesis of the antitumor drug mithramycin by *Streptomyces argillaceus*." 1: J Biol Chem. Feb. 4, 2000;275(5):3065-74.

J. Kantola, et al. "Folding of the polyketide chain is not dictated by minimal polyketide synthase in the biosynthesis of mithramycin and anthracycline." 1: Chem Biol. Oct. 1997;4(10):751-5.

L. Prado, et al. "Oxidative cleavage of premithramycin B is one of the last steps in the biosynthesis of the antitumor drug mithramycin." 1: Chem Biol. Jan. 1999;6(1):19-30.

E. Fernandez, et al. "Identification of two genes from *Streptomyces argillaceus* encoding glycosyltransferases involved in transfer of a disaccharide during biosynthesis of the antitumor drug mithramycin." 1: J Bacteriol. Sep. 1998;180(18):4929-37.

D Rodriguez, et al. "Purification and characterization of a monooxygenase involved in the biosynthetic pathway of the antitumor drug mithramycin." 1: J Bacteriol. Jul. 2003;185(13):3962-5.

D Rodriguez, et al. "MtmMII-mediated C-methylation during biosynthesis of the antitumor drug mithramycin is essential for biological activity and DNA-drug interaction." 1: J Biol Chem. Dec. 5, 2003 [Epub ahead of print].

A. Gonzalez, et al. "The mtmVUC genes of the mithramycin gene cluster in *Streptomyces argillaceus* are involved in the biosynthesis of the sugar moieties." Molecular and General Genetics, (Feb. 2001) vol. 264, No. 6, pp. 827-835. Springer-Verlag, New York.

Lily L. Remsing, et al. "Ketopremithramycins and ketomithramycins, four new aureolic acid-type compounds obtained upon inactivation of two genes involved in the biosysnthesis of the deoxysugar moieties of the antitumor drug mithramycin by *Streptomyces argillaceus*, reveal novel insights into post-PKS tailoring steps of the mithramycin biosynthetic pathway." Journal of the American Chemical Society, (Feb. 27, 2002) 124 (8) 1606-14.

(Continued)

*Primary Examiner*—Rodney P. Swartz
(74) *Attorney, Agent, or Firm*—McDermott Will & Emery LLP

(57) ABSTRACT

The invention, in one aspect, generally relates to mithramycin derivatives from mutated *Streptomyces argillaceus* and their production. The invention also relates using the derivatives for the treatment of various diseases. Finally, the invention relates to a mutated *Streptomyces argillaceus* useful in the production of the mithramycin derivatives.

10 Claims, 6 Drawing Sheets

OTHER PUBLICATIONS

Axel Trefzer, et al. "Rationally designed glycosylated premithramycins: hybrid aromatic polyketides using genes from three different biosynthetic pathways." Journal of the American Chemical Society, (May 29, 2002) 124 (21) 6056-62.

J. Plowman, et al. "Efficacy of the quinocarmycins KW2152 and DX-52-1 against human melanoma lines growing in culture kand in mice." Cancer Research, (Feb. 15, 1995) 55 (4) 862-7.

P. H. Viollier, et al. "Role of acid metabolism in *Streptomyces coelicolor* morphological differentiation and antibiotic biosynthesis." Journal of Bacteriology, (May 2001) 183 (10) 3184-92.

Lily L Remsing, et al. "Inhibition of c-src transcription by mithramycin: structure-activity relationships of biosynthetically produced mithramycin analogues using the c-src promoter as target." Biochemistry, (Jul. 15, 2003) 42 (27) 8313-24.

K. Stajner, et al. "Variability and strain selection in *Streptomyces atroollvaceus*. II. Chromatographic analysis of mithramycin-producing and nonproducing strains." Folla Microbiologica (Prague, Czech Republic) (1974), 19(6), 498-506.

G. Blanco, et al. "Identification of a sugar flexible glycosyltransferase from *Streptomyces olivaceus*, the producer of the antitumor polyketide elloramycin." Chemistry and Biology, (Mar. 2001) 8 (3) 253-63.

M J F Lozano, et al. "Characterization of two polyketide methyltransferases involved in the biosynthesis of the antitumor drug mithramycin by *Streptomyces argillaceus*." Journal of Biological Chemistry, (Feb. 4, 2000) vol. 275, No. 5, pp. 3065-3074. Publisher: Amer Soc Biochemistry Molecular Biology Inc, Bethesda, MD.

Lily L. Remsing, et al. "Mithramycin SK, a novel aureolic acid-type antitumor compound generated by combinatorial biosynthesis, shows an improved therapeutic index compared to mithramycin in in vitro antitumor and toxicity assays." 2003, American Association for Cancer Research. 2003 Proceedings of the AACR <http://aacr03.agora.com/planner/displayabstract.asp?presentationId=9968>.

Sukalyan Chatterjee, PhD, et al. "Sequence-Selective DNA Binding Drugs Mithramycin A and Chromomycin $A_3$ Are Potent Inhibitors of Neuronal Apoptosis Induced by Oxidative Stress and DNA Damage in Cortical Neurons." Annals of Neurology, vol. 49, No. 3, Mar. 2001, Wiley-Liss, Inc., pp. 345-354.

Lily L. Remsing, et al. "Ketopremithramycins and Ketomithramycins, Four New Aureolic Acid-Type Compounds Obtained upon inactivation of Two Genes Involved in the Biosynthesis of the Deoxysugar Moieties of the Antitumor Drug Mithramycin by *Streptomyces argillaceus*, Reveal Novel Insights into Post-PKS Tailoring Steps of the Mithramycin Biosynthetic Pathway." J. Am. Chem. Soc., vol. 124, No. 8, 2002, pp. 1606-1614.

FIG. 6A

SEQUENCE LISTING NO. 1

| | | | | | | |
|---|---|---|---|---|---|---:|
| ggatcctcgt | ccgtctcgac | caccaggtag | cggctcagcg | cccggtagaa | acggccgccc | 60 |
| tcctcggact | gcacggcgtc | gtagaggatc | tgctccggcc | gggccgcgag | cacctggtcc | 120 |
| aggaacctgg | gccgctgttc | ggggggggaga | tgagcgtggt | cgtcggggac | gcactggacg | 180 |
| gtcggggcca | gctcgatgag | gtcgacgtag | cccggttccg | ggtgggcgcg | cgccaggacg | 240 |
| tggaggacgc | cgtcgatccg | cttggccagg | aacgccacca | ccccggtgcc | gcgcgggctg | 300 |
| agcagcggct | gggtccaccc | cttgacttcg | cggttgccgg | cctccacaga | cacggcgacg | 360 |
| atcgcgaagt | gccgtccact | ggtgtggcgt | atctcgtccg | tgtcgcggac | ccagccgtcc | 420 |
| acggaggtca | gcgggacgag | ctgcgcggcg | acctcgctgc | gcgccctgag | cccgttgaac | 480 |
| cagcgcagca | gctcgggcag | ggtgtgcgcg | gcggggcct | gcgcggacag | ggaggcggtc | 540 |
| agggcggcca | cggccgcccc | gcgggaaccg | tcggtcgtga | ctccctcgag | ggaaccgtcc | 600 |
| ggcggggcga | cggggaggca | ggccaggacc | gtccgagtgt | ccatgttgac | caggtccggg | 660 |
| acgccgagca | gccggcggac | ctgaccgagg | gtcagccagc | ggtagtcctc | gtgctcggc | 720 |
| acgtcgccga | cggcctcgac | gacgagattg | cggttgcgtt | tgcggaagaa | ccaggaaccg | 780 |
| tgctcggact | ggagcacgtc | gaccagcggc | cggcccttgc | cggggtccgt | gaagtactcc | 840 |
| aggtaccgca | cggcgctgcc | ctcgtgcacg | cccgtgtagt | tgctgcgggt | ggcctgcacc | 900 |
| gtgggcgaca | actggagtcc | ctcggcgttg | ccgggctcgg | ccttcgcctg | catcaggcag | 960 |
| tgcaggacac | cgtcgaactc | cttgaccagg | atgccgagga | aacccacttc | cggctggtgc | 1020 |
| atgatcggct | gggaccagga | gacggggtcc | gggccctcgg | agcgagcccg | cagcccttcg | 1080 |
| acggtgaaga | agcggccgct | gtcgtgcgcc | agattcccgg | tgaccgggtg | gaagccccag | 1140 |
| cgctggagct | cggcgaaggg | gatgcgcctc | acgtccatcc | ggatggcctt | gcggcgctcc | 1200 |
| tcgaaccagt | cgtggacacc | acccaggggac | agcagtccgc | tgtcggccga | cgccgattcg | 1260 |
| gcgatgcgcc | tcagatccgg | cgcgtcgagg | ccgtccgggg | ggaccgctgg | atgctttctg | 1320 |
| ctcatgatcg | cttgagtcat | ggatgtctct | cccatcgcag | gcatcggcag | cgcgctcggg | 1380 |
| ccaccgtcgg | cacccaggct | ggagtcgcgc | tcgaggcccg | gtcggtccgg | accgggcgga | 1440 |
| cggcggttcc | gtcagggctc | gagccgcctt | cgatcagggc | ggccgaacgt | ggtcgccgtg | 1500 |
| gagttccgaa | gccttggccg | aagtggcctt | tcagtgagtg | agatcgtgta | cggcaacctg | 1560 |
| ctgtacccgc | aggacgacac | ccccgacgag | gtggttctct | cctcgatcag | agcggccctt | 1620 |
| gacgccgggg | tgacgacctt | cgacaccgcg | gacgtctacg | gcatgttccg | ctccgagagc | 1680 |
| ctgctgggcc | gggcactggc | cggcacgccc | cgcgaagagc | tggtgctgtg | caccaaggtg | 1740 |
| gggatgccga | ccggggttcgg | gcccaacgga | cggggggctgt | cgaggaaaca | cgtcatggag | 1800 |
| tccgtcgacg | gctcgctgcg | ccgtctgcgc | gtcgaccaca | tcgacgtcta | caccgcgcac | 1860 |
| cgctacgacc | cggcgactcc | gctggaggag | ctgatgtgga | ccttctccga | cctggtacgg | 1920 |
| gccgggaaga | tcctctacgt | cggcatgtcg | gaatggcccg | tggagcggat | cgccgaggcg | 1980 |
| gccgggatag | gtgcgcggct | cggtgtgccg | gtgatctgtc | acatgccccg | ctactcgatg | 2040 |
| ctgtggcggg | cgccggaggc | cgaggtgatc | cccgcctgcc | gtgacctggg | catcggccag | 2100 |
| atcgggagct | cgaattcgaa | gcttctgcag | ctcacggtaa | ctgatgccgt | atttgcagta | 2160 |
| ccagcgtacg | gcccacagaa | tgatgtcacg | ctgaaaatgc | cggcctttga | atgggttcat | 2220 |
| gtgcagctcc | atcagcaaaa | ggggatgata | agtttatcac | caccgactat | ttgcaacagt | 2280 |
| gccgttgatc | gtgctatgat | cgactgatgt | catcagcggt | ggagtgcaat | gtcgtgcaat | 2340 |
| acgaatggcg | aaaagccgag | ctcatcggtc | agcttctcaa | ccttggggtt | accccggcg | 2400 |
| gtgtgctgct | ggtccacagc | tccttccgta | gcgtccggcc | cctcgaagat | gggccacttg | 2460 |
| gactgatcga | ggcctgcgt | gctgcgctgg | gtccgggagg | gacgctcgtc | atgcctcgt | 2520 |
| ggtcaggtct | ggacgacgag | ccgttcgatc | ctgccacgtc | gcccgttaca | ccggaccttg | 2580 |
| gagttgtctc | tgacacattc | tggcgcctgc | caaatgtaaa | gcgcagcgcc | catccatttg | 2640 |
| cctttgcggc | agcggggcca | caggcagagc | agatcatctc | tgatccattg | cccctgccac | 2700 |
| ctcactcgcc | tgcaagcccg | gtcgcccgtg | tccatgaact | cgatgggcag | gtacttctcc | 2760 |

FIG. 6B

| | | | | | | |
|---|---|---|---|---|---|---|
| tcggcgtggg | acacgatgcc | aacacgacgc | tgcatcttgc | cgagttgatg | gcaaaggttc | 2820 |
| cctatggggt | gccgagacac | tgcaccattc | ttcaggatgg | caagttggta | cgcgtcgatt | 2880 |
| atctcgagaa | tgaccactgc | tgtgagcgct | ttgccttggc | ggacaggtgg | ctcaaggaga | 2940 |
| agagccttca | gaaggaaggt | ccagtcggtc | atgcctttgc | tcggttgatc | cgctcccgcg | 3000 |
| acattgtggc | gacagccctg | ggtcaactgg | gccgagatcc | gttgatcttc | ctgcatccgc | 3060 |
| cagagggcgg | gatgcgaaga | atgcgatgcc | gctcgccagt | cgattggctg | agctcatgag | 3120 |
| cggagaacga | gatgacgttg | gaggggcaag | gtcgcgctga | ttgctgggc | aacacgtgga | 3180 |
| gcggatcggg | gattgtcttt | cttcagctcg | ctgatgatat | gctgacgctc | aatgccgttt | 3240 |
| ggcctccgac | taacgaaaat | cccgcatttg | gacggctgat | ccgattggca | cggcggacgg | 3300 |
| cgaatgcgg | agcagacgct | cgtccggggg | caatgagata | tgaaaaagcc | tgaactcacc | 3360 |
| gcgacgtctg | tcgagaagtt | tctgatcgaa | aagttcgaca | gcgtctccga | cctgatgcag | 3420 |
| ctctcggagg | gcgaagaatc | tcgtgctttc | agcttcgatg | taggagggcg | tggatatgtc | 3480 |
| ctgcgggtaa | atagctgcgc | cgatggtttc | tacaaagatc | gttatgttta | tcggcacttt | 3540 |
| gcatcggccg | cgctcccgat | tccggaagtg | cttgacattg | gggaatttcg | acgtcatatg | 3600 |
| gatccgatga | tctgctactt | caccctggaa | cagggcgtgc | tgacgggcaa | gtacgcgccg | 3660 |
| ggcgccccgc | ccccggccgg | gtcccgggcc | acggcaccca | aaggtggccg | ggcccgttg | 3720 |
| atgcggcgct | ggctggacga | cgacaaggtc | ctcgggcgcg | tcgagcggct | gcgtccgctc | 3780 |
| gccgaggagg | ccgggctgac | cacggcgcac | ctcgcgtggg | tgctccagaa | tcccgccgtc | 3840 |
| agcggggccg | tcatcggctc | gttcaacgcc | gaacaggtcc | tggccaacgc | cgagtcggcc | 3900 |
| ggcgtccgtc | tggagacgga | cctgctggtg | aggatcgacg | aggtcctggg | cgactccgtc | 3960 |
| gtgcacgacg | aggagtagcc | cccgggcggg | gccggtggag | gcggatgcga | cgccgttcgt | 4020 |
| tccgggggct | gccgtccgtt | ccggttcggc | gacggaggcg | gatgcatccg | cgcccgtccg | 4080 |
| gcccaccgcc | cggcccgccc | ggcatgccgg | gcgcggggt | cgggcaccga | ggtgcaagcg | 4140 |
| ccccgaccgt | acgccgagcc | gagccgaccc | gtggcctctc | ccgtccctcc | tgaccgaccc | 4200 |
| tcccccctccc | tcgtccttgc | cgacaggttc | gccctactt | ccgacgctcc | cggagaggtc | 4260 |
| cactacggat | gcgcattctg | ttcaccacgt | tcccctggca | ctcccatcac | ttcccgatgg | 4320 |
| tcccactgga | gcggcggcgc | tggccgccgg | gcatgaggtg | cgggtcgcga | gcgcgcccgc | 4380 |
| gctgatgccg | gtcgtgaccg | cgtccggcct | gcccgggata | ccggtcggcc | aggacgtgga | 4440 |
| ccttgcctcc | ctgtccaacg | accgcagccg | ggccgcctgg | cacgttcagg | accgctggcc | 4500 |
| cgacgactgg | cccgtccgtc | cggaactcct | cgacgacgag | cagttcgcgc | tgatcgagaa | 4560 |
| cctgggacgg | atgcagacgg | tcatggcctc | ggccatgctc | gacgaccCgc | tgagcttcgc | 4620 |
| ccggtactgg | cggcccgacc | tggtggCgca | cgacgccgtc | agcctcgccg | gcccggtggt | 4680 |
| cgccgccgcg | ctgggcgtgc | ccaacgtcag | ccacctgtgg | ggcactccgg | gactccagcg | 4740 |
| catcgagctg | cgccgcatgg | gcggcgaacc | gctgccggag | tacgtccggc | tgtacgagcg | 4800 |
| ggcgggaacg | acggtgcgga | ccgagcccag | tgcctggatc | gaccccagtg | ccccggcat | 4860 |
| ccggtacccg | gccggaccga | cctgccgtca | gatgcggtac | gtgccctaca | acggcccggg | 4920 |
| cctgctgccg | gactggctgc | gccgggaacc | gtcgggcagc | cgggtctgcg | tcacgtgggg | 4980 |
| cgccacctcc | atggccctgc | gcggcggcac | cgtcgtcgaa | ctcgtacgcc | agtgcgtgga | 5040 |
| agccgccgcc | gaggtggccg | acgaggtcgt | cgtcgcggtg | accgaacaga | ccgcgcgggc | 5100 |
| gctggaggac | acgccgctgc | cggaccacgc | acgcgtcgcg | gtcggattgc | cgctgcacct | 5160 |
| gctggtgccg | tcctgcgacc | tcgtggtcca | ccacggtggc | gccggcacca | gcatgaccgc | 5220 |
| cgcggtcgcg | ggcgtacgac | agctgctgat | caccacccgg | cccgagccca | cggtcaacgg | 5280 |
| cacccggctg | gccgcgtcgg | gcgccgcccg | gcacctgatg | accacggagg | tccccgccgc | 5340 |
| ccgggaggga | gtgctgctgc | tgcgcgccga | gatggaccgt | ctcctatcgg | accccgcaca | 5400 |
| cggcgccgcc | gcgcggcggc | tggccgacgg | catccgcacc | cagcccgcac | cggccgacgt | 5460 |

FIG. 6C

```
ggtggcggag  ctgacgcatc  tcgtccggta  ggtcgatccc  gcccggaagg  gatgaatctc  5520
gcccggcggg  gacgactccc  gcccgacagg  aggagcaaga  accatgcgcg  ttctggtgac  5580
cacgtccccg  tggcccaccc  attacttcgt  cgtccagccg  ctggccgccg  cgttccgcgc  5640
ggcgggccac  gaagtcctcg  tggcggccca  gccgtccatg  gcggacctgg  tcacccggtc  5700
cggcctgccc  atggccgccg  tcggcagcga  catcgacatg  gtggacatcc  gccgcaagac  5760
gctctcccag  gaactggacg  cccgtcagaa  gcccggggaa  cccgcccggg  ccgacgacgg  5820
cggtcaggtc  ttcgacacct  ggcagcaggc  caccctcgcc  aacctcgacc  cggtcatgga  5880
cctcgcccgg  acctggaaac  cggacctggt  gctcgccgac  accatgtgcc  cgccgggcct  5940
cgtcgccgca  caggaactcg  gcgtgccggg  gatcc                              5975
```

DERIVATIVES OF MITHRAMYCIN AND METHODS OF MAKING AND USES THEREOF

CROSS REFERENCE TO RELATED APPLICATIONS

This application claims the benefit of priority of Provisional Application No. 60/548,175, filed Mar. 1, 2004 which is incorporated herein by reference.

STATEMENT OF U.S. GOVERNMENT SPONSORED RESEARCH

A portion of this invention was made with U.S. government support under a grant from the National Institutes of Health (NIH), Grant No. RO1CA91901. The government may have certain rights in this invention.

Mithramycin (MTM) is an aureolic acid-type polyketide produced by various soil bacteria of the genus *Streptomyces*, including *Streptomyces argillaceus* ATCC 12956 (deposited with ATCC, P.O. Box 1549, Manassas, Va. 20108 USA). MTM has the following formula (I):

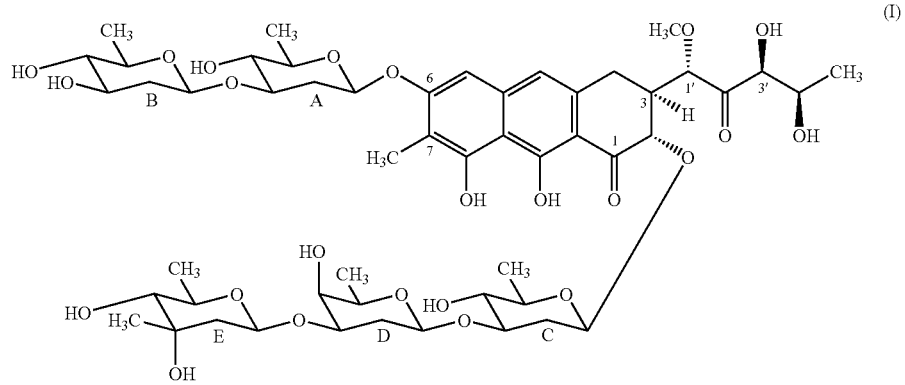

MTM is the most important representative of the aureolic acid group of antitumor agents, and is used to treat testicular carcinoma, Paget's disease and hypercalcemia caused by malignancy-associated bone lesions. MTM is also an agent for neuroprotection in the treatment of neurological diseases such as stroke, amyotropic lateral sclerosis, Parkinson's disease, Huntington's disease, multiple sclerosis and viral encephalitis.

The aureolic acid group of compounds includes MTM, chromomycin A3 (CHR), olivomycin A (OLI), UCH9, and durhamycin A. All contain the same tricyclic core moiety with a unique dihydroxy-methoxy-oxo-pentyl side chain attached at carbon 3 and vary only slightly, with respect to the residue at carbon 7, which is either a H atom or a small alkyl side chain. However, these naturally occurring aureolic acid antibiotics differ in the nature and linking of their saccharide chains, which consist of various 2,6-dideoxysugar residues. Such structural variations impart subtle differences in the DNA binding and activity profiles among the members of this group.

The biosynthetic gene cluster leading to the formation of MTM has been studied and resulted in the identification of 34 genes and the assignment of various gene product functions for the biosynthesis of MTM. FIG. 1 shows the gene organization of the MTM biosynthetic gene cluster in *Streptomyces argillaceus*. MTM biosynthesis proceeds through tetracyclic intermediates with glycosylation steps occurring on the tetracyclic biosynthetic intermediates. One of the last steps, the key step in MTM biosynthesis, is the oxidative cleavage of the fourth ring of the fully glycosylated tetracyclic intermediate premithramycin B, which results in the formation of a tricyclic immediate precursor of MTM. FIG. 2 shows the rearrangement of the tetracyclic structure into the tricyclic structure found in MTM. This rearrangement is very important step because it causes an alteration of the shaping of the molecule. Only the tricyclic structure is biologically active. In conjunction with the oxidative cleavage step is a decarboxylation step that occurs. A pentyl side chain attached at carbon 3 is generated, which plays an important role for the biological activity of the aureolic acid class of antitumor agents. To generate the final MTM molecule, the oxidative cleavage step is followed by a ketoreduction step, in which the keto group in the 4'-position of the 3-side chain is reduced to a secondary alcohol.

The present invention provides for a mutant *Streptomyces argillaceus* (*S. argillaceus* M7W1) lacking a nucleic acid that encodes an active ketoreductase. The mutant *S. argillaceus* M7W1 produces mutant derivatives: demycarosyl-mithramycin-SK, mithramycin-SA, mithramycin-SDK and mithramycin-SK, the latter being the major product. The derivatives are antitumor agents and also act as neuroprotective agents in the treatment of neurological diseases.

SUMMARY OF THE INVENTION

The invention generally relates to the production of mithramycin derivatives from a mutant *S. argillaceus* M7W 1, lacking a nucleic acid that encodes an active ketoreductase.

The present invention also provides for a mutant *S. argillaceus* M7W1 produced by mutating an mtmW gene of *Streptomyces argillaceus*, whereby the mutated gene does not encode active ketoreductase.

The present invention further provides a method of making a mutant *S. argillaceus* M7W1 comprising mutating an mtmW gene of *S. argillaceus* to produce a mutated gene by insertional mutation of the mtmW gene, whereby the mutated gene does not encode active ketoreductase. The mtmW is mutated ex vivo, and is used to replace the wild type mtmW gene of *Streptomyces argillaceus*.

Finally, the invention relates to mutated organisms useful in the production of mithramycin derivatives: demycarosyl-mithramycin-SK, mithramycin-SA, mithramycin-SDK and mithramycin-SK.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

FIGS. 6A, 6B and 6C are the sequence listing for a gene containing aac(3)IV and mtmW genes (SEQ ID NO:1).

DETAILED DESCRIPTION OF THE INVENTION

Figure 1:
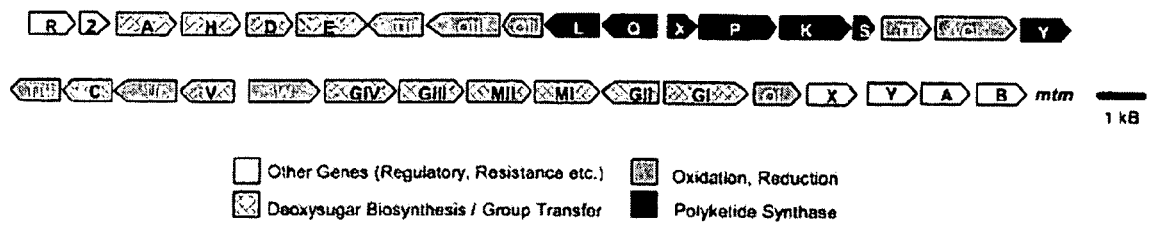
FIG. 1 is the gene organization of the MTM biosynthetic gene cluster in Streptomyces argillaceus.
Figure 2:
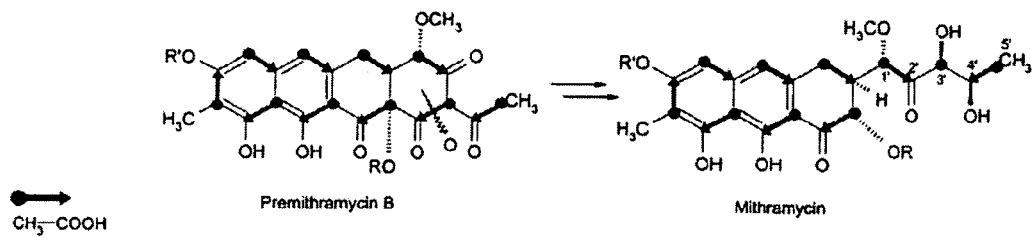
FIG. 2 shows the rearrangement of the tetracyclic rings to form MTM.

The present invention may be understood more readily by reference to the following detailed description of preferred embodiments of the invention and the examples included therein and to the drawing figures and their previous and following description. As used in the specification and the appended claims, the singular forms "a," "an" and "the" include plural referents unless the context clearly dictates otherwise. Thus, for example, reference to "a pharmaceutically acceptable carrier" includes mixtures of two or more such carriers, and the like.

The gene replacement step of the present invention involves standard nucleic acid manipulations well known to the skilled artisan. "Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to the sequence which is naturally occurring or may include alternative codons which encode the same amino acid as that which is found in the naturally occurring sequence. Furthermore, nucleic acids may include codons which represent conservative substitutions of amino acids as are well known in the art.

The isolation of nucleic acids can therefore be accomplished by techniques such as cell lysis followed by phenol plus chloroform extraction, followed by ethanol precipitation of the nucleic acids. The nucleic acids of this invention can be isolated from bacterial cells, for example, Streptomyces argillaceus, according to methods well known in the art for isolating nucleic acids. Alternatively, the nucleic acids of the present invention can be synthesized according to standard protocols well described in the literature for synthesizing nucleic acids. Modifications to the nucleic acids of the invention, for example, the mtmW gene which encodes an active ketoreductase, will decrease the activity of the enzyme or block or reduce its synthesis.

A nucleic acid containing a promoter or other regulatory sequence and/or encoding a protein (e.g., antibiotic resistance factor or enzyme) of this invention can be part of a recombinant nucleic acid construct comprising any combination of restriction sites and/or functional elements as are well known in the art which facilitate molecular cloning and other recombinant DNA manipulations. Thus, the present invention further provides a recombinant nucleic acid construct comprising a nucleic acid encoding an enzyme to be modified or deleted by this invention.

The nucleic acid sequences can be expressed in hosts, for example, Streptomyces argillaceus, after the sequences have been positioned to ensure the functioning of an expression control sequence. Host cells of the present invention are transformed and cultured in conventional nutrient media modified as appropriate for inducing the various promoters if induction is carried out. "Transformation" means introducing DNA into an organism so that the DNA is replicable, either as an extra-chromosomal element or as chromosomal integration. Depending on the host cell used, transformation is done using standard techniques appropriate to such cells.

A "cell" can be a cell from any organism including, but not limited to, a bacterium. Bacterial cells of this invention are cultured in suitable media in which the promoters can be induced using standard techniques. Any other necessary supplements besides carbon, nitrogen, and inorganic phosphate sources may also be included at appropriate concentrations, introduced alone or as a mixture with another supplement or medium such as a complex nitrogen source.

The present invention provides a method of inhibiting growth of a tumor, comprising contacting the tumor with a compound of the invention. As used herein, "inhibiting" means decreasing, slowing or stopping. Thus, a compound of this invention can decrease, slow or stop the growth of a tumor cell. As used herein, "growth" means increase in size or proliferation or both. Thus, a compound of this invention can inhibit a tumor cell from becoming larger and/or can prevent the tumor cell from dividing and replicating and increasing the number of tumor cells. A "tumor cell" is a cell comprising a neoplasm (new growth), which can be cancerous (malignant) or non-cancerous (benign). A cancerous tumor cell can invade surrounding normal tissues and blood/lymph vessels and metastasize to tissues distant from the original tumor. In contrast, a non-cancerous tumor cell can grow and compress surrounding normal tissue but cannot invade normal tissues and blood/lymph vessels nor metastasize to tissues distant from the original tumor.

A cell can be in vitro. Alternatively, a cell can be in vivo and can be found in a subject. A "cell" can be a cell from any organism including, but not limited to, abacterium. As used throughout, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

The present invention provides a method of treating cancer in a subject diagnosed with cancer, comprising administering to the subject an effective amount of a compound of the invention in a pharmaceutically acceptable carrier, whereby the compound treats the cancer in the subject. In general, an "effective amount" of a compound is that amount needed to achieve the desired result or results. For example, an effective amount of a compound of the present invention treats the cancer by inhibiting the growth of the cells comprising the tumor, thereby preventing invasion of normal tissues and blood/lymph vessels by the tumor cells, thus preventing metastases. Examples of cancers that can be treated include, but are not limited to, lung, colon, ovarian, prostate, testicular, melanoma, kidney, breast, central nervous system and leukemia. By "pharmaceutically acceptable" is meant a material that is not biologically or otherwise undesirable, i.e., the material may be administered to an individual along with the selected compound without causing substantial deleterious biological effects or interacting in a deleterious manner with any of the other components of the composition in which it is contained.

The invention is directed to modifying the post-polyketide synthase (post-PKS) tailoring steps of the mithramycin biosynthesis by *Streptomyces argillaceus*, in particular, the ketoreductase encoding genes. The ketoreductase step within the pentyl side chain attached at carbon 3 to MTM side chain is the last step of the mithramycin biosynthesis. The mtmW gene is the enzyme that catalyzes the ketoreduction step affecting the 3-side chain in the mithramycin biosynthesis.

Figure 3:
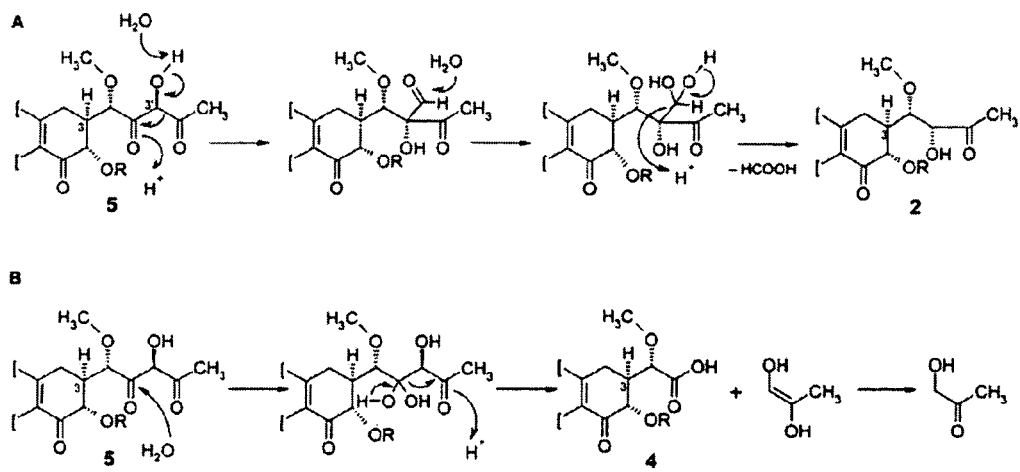
FIG. 3 shows a non-enzymatic Favorskii-type rearrangement in the formation of mithramycin SK and mithramycin SA.

The mtmW gene is located ca. 8 kb downstream of the mithramycin PKS genes. The gene is replaced by an aac(3)IV gene that yields a *S. argillaceus* mutant, which produces four new mithramycin derivatives, namely mithramycin-SK, demycarosyl-mithramycin-SK, mithramycin-SA, mithramycin-SDK. Mithramycin-SK is the major product. The structures of mithramycin-SK and demycarosyl-mithramycin-SK bear a butyl side chain attached at carbon 3 instead of the expected pentyl side chain with an additional keto function. This can be explained through a non-enzymatic Favorskii-type rearrangement of the initially formed pentyl side chain with two keto groups in β-position to each other. FIG. 3 shows the non-enzymatic Favorskii-type rearrangement in the formation of mithramycin-SK and mithramycin-SA having structures 2 and 4, respectively, from MTM having structure 5.

The invention contemplates mutant MTM derivatives having the following general formula (II):

art. Examples of many of the possible groups can be found in "Protective Groups in Organic Synthesis" by T. W. Green, John Wiley and Sons, 1981, which is incorporated herein by reference in its entirety.

The protecting group comprises, but is not limited to, an alkyl group, a cycloalkyl group, a heterocyloalkyl group, a hydroxyalkyl group, a halogenated alkyl group, an alkoxyalkyl group, an alkenyl group, an alkynyl group, an aryl group, a heteroaryl group, an aralkyl group, an ester, a carbonate group, a carboxylic acid, an aldehyde, a keto group, an ether group, a urethane group, a silyl group, a sulfo-oxo group, or any combination thereof. In one embodiment, when $R^{11}$ in formula (II) is a protecting group, the protecting group is an alkyl group such as methyl, ethyl, propyl, isopropyl, butyl, isobutyl, or pentyl. In another embodiment, some the hydroxyl groups in formula (II) may be protected while others are not. For example, $R^1$, $R^2$, $R^3$, $R^4$, $R^5$, $R^6$, $R^7$, $R^8$, $R^{13}$ and $R^{14}$ may be not protected while $R^{11}$ is protected by an alkyl group selected from the group consisting of methyl, ethyl, propyl, isopropyl, butyl, isobutyl and pentyl.

The protecting groups are removable from the product compounds of the invention, to regenerate the hydroxyl group by methods known in the art. Methods for removing protect-

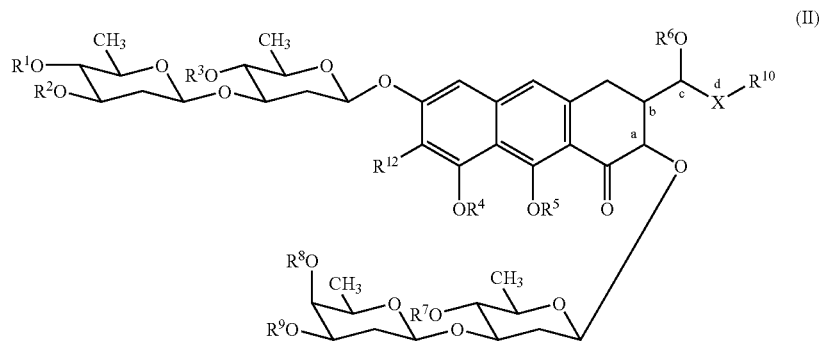

(II)

wherein $R^1$, $R^2$, $R^3$, $R^4$, $R^5$, $R^6$, $R^7$ and $R^8$ are each, independently, hydrogen or a protecting group;

X is C=O or CH($OR^{11}$), wherein $R^{11}$ is hydrogen or a protecting group;

$R^{10}$ is OH when X is C=O or C(O)CH$_3$ when X is CH($OR^{11}$);

$R^9$ is hydrogen, a protecting group or

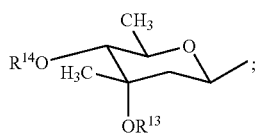

$R^{12}$ is methyl or hydrogen; and the stereochemistry at carbons a, b and c is R, S or mixtures thereof, and when X is CH($OR^{11}$), the stereochemistry of d is R or S.

One or more of the hydroxyl groups present in the mutant derivative can be protected with a protecting group. The term "protecting group" is defined herein as a group that is used to replace hydrogen of a hydroxyl group to produce a new group. Various protecting groups useful in the invention and methods for their synthesis and removal are well known in the ing groups include, but are not limited to, hydrolysis, hydrogenolysis, treatment with acids or bases, and the like.

The stereocenters a, b and c in formula (II) can be R, S or mixtures thereof. The term "mixtures thereof" with respect to the stereochemistry of a-c, when considered with stereocenter d, includes all possible diastereoisomers and enantiomers of formula (II). A compound having the formula (II) can be a racemic mixture or exist as an enantiomeric excess of a particular stereochemistry. Alternatively, a compound having the formula (II) can exist as two or more diastereoisomers. For example, the stereochemistry at carbons a, b and c are S and the stereochemistry at carbon d is R or the compounds having the formula (II) can be enantiomerically pure.

Using techniques known in the art, it is possible to epimerize the stereocenters a-d. A compound having the formula (II) can be treated with a base in order to produce a racemic or diastereomeric mixture. Also, the use of a chiral auxiliary in combination with a base can be used to selectively convert stereocenters a-d from one stereoisomer to the other.

The mutant *S. argillaceus* M7W1 produces five new derivatives of MTM: mithramycin-SK, demycarosyl-mithramycin-SK, mithramycin-SA and mithramycin-SDK. Mithramycin-SK has the following formula (III):

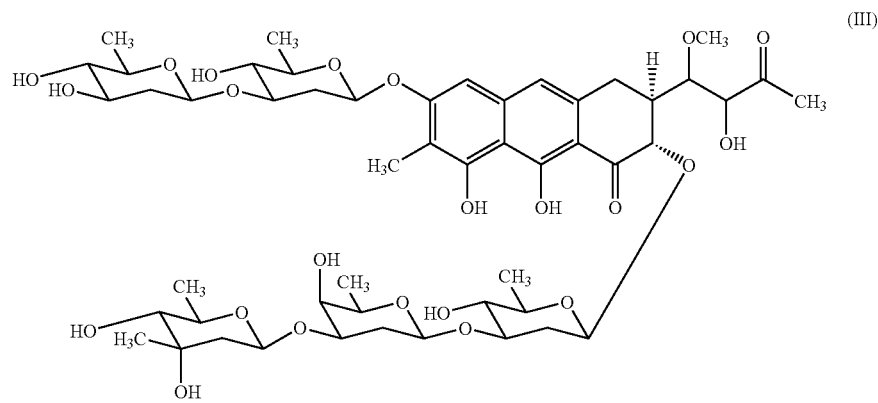
(III)
In a preferred embodiment, the stereochemistry at carbons a, b and c is S and the stereochemistry at d is either R or S. The methyl group on the first aromatic ring of mithramycin-SK can be a H, thereby providing another derivative of formula (III).
Demycarosyl-mithramycin-SK has the following formula (IV):
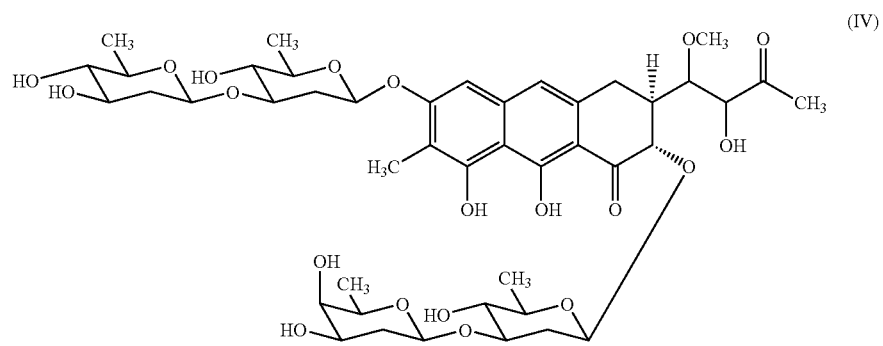
(IV)
Mithramycin-SA has the following formula (V):
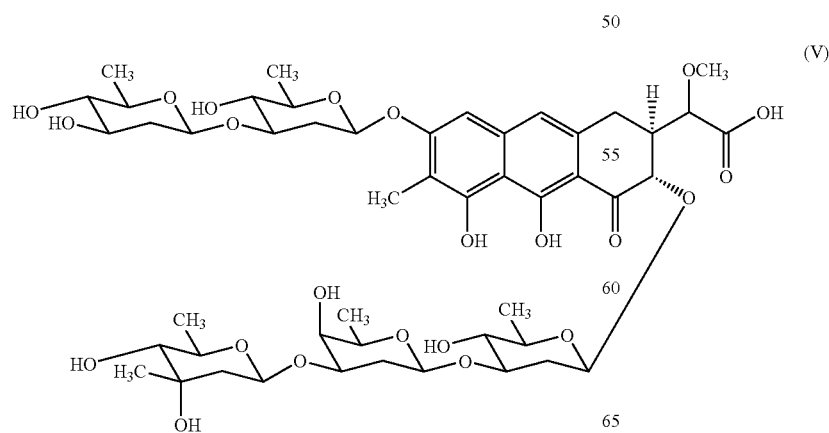
(V)

Mithramycin-SDK has the following formula (VI):

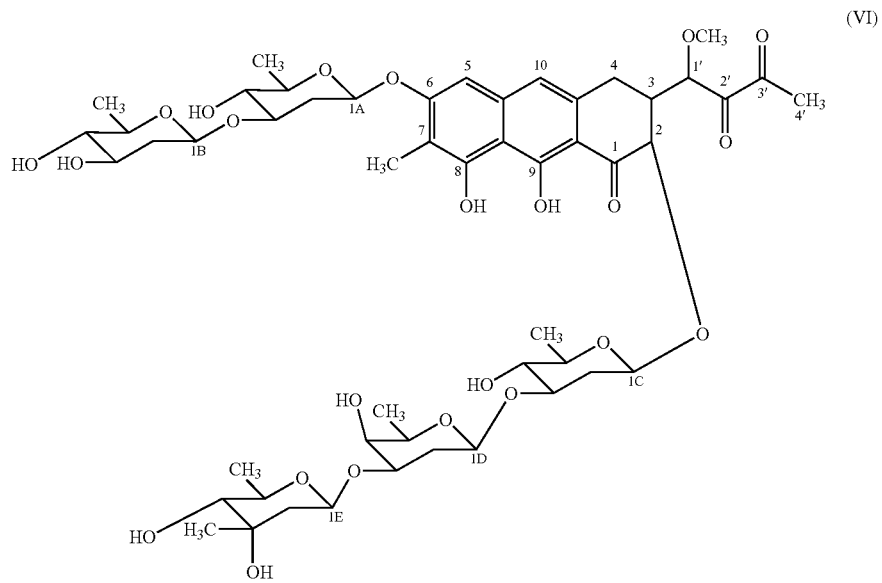

The method for making and isolating derivatives mithramycin-SK, mithramycin-SA, demycarosyl-mithramycin-SK, and mithramycin-SDK, generally involves (i) incubating the mutant *S. argillaceus* M7W1, (ii) forming a composition and (iii) isolating the derivatives from the composition. The incubation time and temperature will vary depending upon the amount of mutant that is employed. The incubation temperature is generally from 25° C. to 40° C., from 30° C. to 35° C., and preferably 30° C. The incubation time ranges from generally several hours to several days, e.g., from 1 to 10 days, 2 to 9 days, 3 to 8 days, 4 to 7 days, and 5 to 6 days.

The mutant *S. argillaceus* M7W1 is generally incubated in a solution. An example of a solution useful includes, but is not limited to, a broth containing the minimal factors required for *S. argillaceus* M7W1 survival or growth. After incubation, the composition is centrifuged, and the supernatant is applied to a solid-phase extraction cartridge to isolate the derivatives. The derivatives can be further purified using techniques known in the art.

Generation of the Mutant *S. argillaceus* by Gene Replacement

The mutant *S. argillaceus* M7W1 is prepared in the following manner. *Streptomyces argillaceus* ATCC 12956 was used as the source of chromosomal DNA. For sporulation on a solid medium, it was grown at 30° C. on plates containing medium A. For protoplast transformation, it was grown in a YEME medium containing 17% sucrose. For growth in a liquid medium, *Streptomyces argillaceus* was grown in a TSB medium (trypticase soya broth, Oxoid). *Escherichia coli* XL1blue was used as the host for plasmid propagation. Methods of preparation and transformation of *Streptomyces argillaceus* protoplasts are taught by T. Kieser et al., in "Practical *Streptomyces* Genetics," published in 2000 by the John Ines Foundation of Norwich, England. This reference is incorporated herein in its entirety.

When plasmid-containing clones were grown, the medium was supplemented with the appropriate antibiotics: thiostrepton, 25 µg/mL; tobramycin, 20 µg/mL; ampicillin, 100 µg/mL; or apramycin, 25 µg/mL. Plasmids pBSKT, pIJ2921, pIAGO, and pEFBA were used (the pEFBA plasmid is a pBSK derivative containing an apramycin resistance cassette; pBSK can be obtained from Stratagene, 11011 M. Torrey Pines Road, La Jolla, Calif.). Plasmid DNA preparations, restriction endonuclease digestions, alkaline phosphatase treatments, ligations, Southern hybridization, and other DNA manipulations were performed according to standard procedures for *E. coli* and *Streptomyces*.

DNA sequencing was performed on double-stranded DNA templates using the dideoxynucleotide chain-termination method. Both DNA strands were sequenced with primers supplied in the kits or with internal oligoprimers (17-mer) using an ALF-express automatic DNA sequencer (Pharmacia Biotech). Computer-aided database searching and sequence analyses were conducted using the University of Wisconsin Genetics Computer Group programs package (UWGCG) and the BLAST program.

Figure 4:
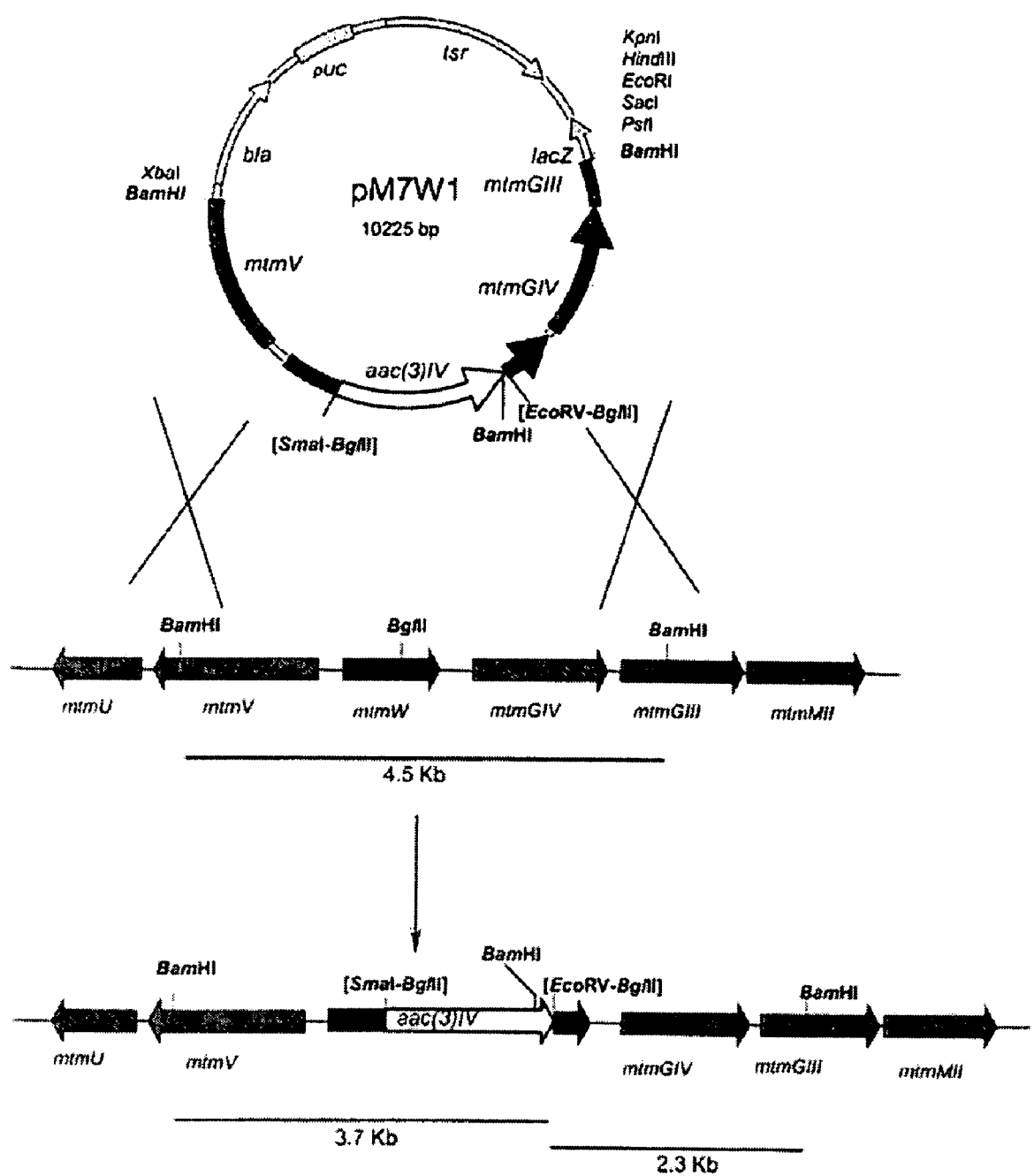
FIG. 4 is a schematic representation of the gene replacement experiment for generating the mutant S. argillaceus M7W1.

A schematic representation of the gene replacement procedure generating mutant *S. argillaceus* M7W1 is shown in FIG. 4. The 1.4 kb region of the mtmW gene is located between several sugar biosynthetic genes (mtmV, mtmU, mtmC, and mtmTS1) and glycosyltransferase genes (mtmGIV and mtmGIII). The sequence of the mtmW gene has been deposited at the EMBL bank (European Molecular Biology Laboratory, Meyerhof Strasse 1, 69117 Heidelberg, Germany) on Apr. 29, 2002, with the accession number AJ459240.

The mtmW gene is comprised of 981 nucleotides with a GTG start codon and a TAG stop codon and codes for a polypeptide of 326 amino acids with an estimated Mr of 35 304. This codon region shows the high GC content and bias for the third codon position, which is characteristic of *Streptomyces* genes. Comparison of the deduced product of mtmW with other proteins using protein databases revealed similarities with various oxidoreductases. The highest similarities were observed with a putative potassium channel beta subunit of *Deinococcus* radiodurans (40% identical amino acids). It also showed similarity with the EryBII (33% identical amino acids) and TylCII (33% identical amino acids) proteins. These two proteins are oxidoreductases, which participate in deoxygenation steps during the biosynthesis of the deoxysugars that form part of the macrolide antibiotics erythromycin and tylosin, respectively.

The mtmW is inactivated by gene replacement through the insertion of an apramycin resistance cassette. To inactivate the mtmW gene, a 4.5 kb BamH1 fragment containing mtmW, mtmGIV, and portions of adjacent genes is subcloned into the BamH1 site of pBSKT, generating M7W0. Upon transformation of the wild-type *Streptomyces argillaceus* ATCC 12956 with pM7W1, transformants were selected for their resistance to apramycin. An apramycin resistance cassette containing the aac(3)IV gene was subcloned as a 1.5 kb SmaI-EcoRV fragment into the unique BgIII site (blunt-ended) located within the coding region for mtmW and oriented in the direction of transcription of mtmW, thus generating mutant *S. argillaceus* M7W1.

The aac(3)IV gene is deposited at Gen Bank having accession numbers X01385 and V01499. The sequence listing containing the aac(3)IV and mtmW genes is set forth in FIG. 6 as SEQ ID NO:1. Nucleotides 1416 to 4221 of SEQ ID NO:1 represent the mutated mtmW gene while nucleotides 2104-3608 of SEQ ID NO:1 represent the aac(3)IV cassette. This construct, pM7W1, was used to transform protoplasts of *Streptomyces argillaceus*, and these transformants were selected for resistance to apramycin. Any antibiotic resistance gene can be used provided that it can be selected for resistance in *Streptomyces argillaceus*. Examples include, but are not limited to, erythromycin, hygromycin, thiostrepton, spectinomycin, viomycin and kanamycin.

To verify that gene replacement occurred, the transformants were tested for their susceptibility to thiostrepton. The wild-type region of the chromosome was replaced by the in vitro mutant *S. argillaceus* M7W1 through a double crossover at both sides of the apramycin cassette. The mutant *S. argillaceus* M7W1 is sensitive to thiostrepton, the consequence of a double crossover, which results in the replacement of the wild-type gene by the in vitro mutated one. This fact was confirmed by Southern hybridization: the 4.5 kb BamH1 fragment of the wild-type strain was replaced by two new BamW fragments of 3.7 and 2.3 kb, as expected if the replacement occurred. It was also confirmed that the gene replacement only affected mtmW, because expressing this gene in trans, using pAGW, restored MTM production in mutant *S. argillaceus* M7W1.

Production and Isolation of Mithramycin-SK, Mithramycin-SA and Demycarosyl-Mithramycin-SK The derivatives mithramycin-SK, mithramycin-SA and demycarosyl-mithramycin-SK were prepared in the following manner. A seed culture was prepared using TSB inoculated with spores of *S. argillaceus* M7W1 and incubated in an orbital shaker for 24 hours at 30° C. and 250 rpm. This seed culture was used to inoculate (at 2.5% v/v) eight 2-liter Erlenmeyer flasks, each containing 400 mL of R5A medium. The flasks were incubated for 5 days under the previously described conditions. The entire culture obtained was centrifuged (12,000 rpm, 30 minutes), the pellets were discarded, and the supernatant was filtered using membrane filters with a pore size of 0.45 µm. The filtrate was applied to a solid-phase extraction cartridge (Supelclean LC-18, 10 g, Supeico), and the retained material was eluted with a mixture of methanol and water. A linear gradient from 0% to 100% methanol over 60 min, at 10 mL/min, was used.

Fractions were taken every 5 minutes. The new derivatives were found in fractions eluted between 40 and 55 minutes. These fractions were evaporated under vacuum, redissolved in a mixture of dimethyl sulfoxide and methanol (50:50), and chromatographed using a µBondapak C18 preparative column (PrepPak Cartridge, 25 mm×100 mm, Waters), with acetonitrile (ACN) and water as solvents, at a flow rate of 10 mL/min. A linear gradient from 30% to 50% ACN in 30 minutes was used. The elutant was further purified under isocratic conditions with 37.5% ACN in water as a solvent. The isolated products were finally dried in vacuo and weighed. Two compounds isolated and purified were mithramycin-SK and demycarosyl-mithramycin-SK, the mithramycin-SK being the major product produced.

An alternative procedure via liquid extraction and conventional chromatography yielded mithramycin-SA in addition to mithramycin-SK and demycarosyl-mithramycin-SK. The procedure is described as follows. A seed culture was prepared using TSB inoculated with spores of *S. argillaceus* M7W1 and incubated in an orbital shaker for 24 hours at 30° C. and 250 rpm. This seed culture was used to inoculate (at 2.5 v/v) sixteen 250-mL Erlenmeyer flasks, each containing 100 mL of modified R5 medium. Thirty-two hours after the inoculation, a pulse feeding of sodium acetate was started and continued for 36 hours at 12 hour intervals (four feedings for a total of 1 g of sodium acetate per liter of culture). The culture was then grown for an additional 52 hours, for a total of 120 hours before extraction. Following acidification with HCl to pH 5.5, the culture was extracted first with EtOAc and then with BuOH.

The more-lipophilic compounds, mithramycin-SK (yield of 13.7 mg) and demycarsoyl-mithramycin-SK (yield of 3.2 mg), were found in the EtOAC extract, whereas the more-hydrophilic mithramycin-SA (yield of 4.8 mg) was solely found in the n-BuOH extract. Silica gel chromatography was used for both the EtOAc extract and the n-BuOH extract. Mithramycin-SK and demycarosyl-mithramycin-SK were purified using an RP-18 silica gel column, followed by Sephadex-LH 20 chromatography. Mithramycin-SA was purified through preparative thin-layer chromatography (TLC), using RP-18 silica gel plates. The exact isolation procedure is described Remsing et al., *J. Am. Chem Soc.*, Vol. 125, No. 19, pp. 5745 to 5753 which is incorporated herein by reference.

An analog of mithramycin-SK having the following formula (VII) can be produced from mutant *S. argillaceus* M7W1:

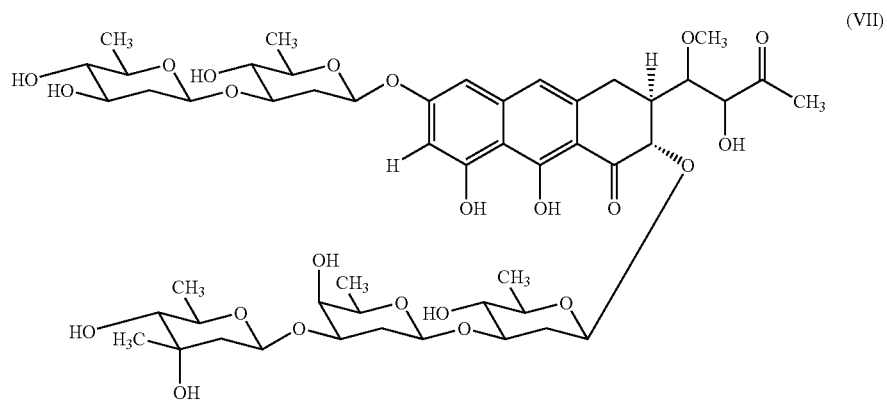
(VII)

This compound can be prepared by inactivating the respective methyltransferase gene in *S. argillaceus* M7W1. The techniques inactivating the respective methyltransferase gene are disclosed in Fernandez-Lozano et al. in "Characterization of Two Polyketide Methyltransferases Involved in the Biosynthesis of the Antitumor Drug Mithramycin by *Streptomyces argillaceus*," *J. Biol. Chem.* 200, 275, 3065-3074 (2000), and Remsing et al. in "Ketopremithramycins and Ketomithramycins, Four New Aureolic Acid-Type Compounds Obtained upon Inactivation of Two Genes Involved in the Biosynthesis of the Deoxysugar Moieties of the Antitumor Drug Mithramycin by *Streptomyces Argillaceus*, Reveal Novel Insights into Post-PKS Tailoring Steps of the Mithramycin Biosynthetic Pathway", *J. Am. Chem Soc.*, Vol. 124, No. 8, 1606-1614 (2002), which are incorporated by reference in their entireties. The methyltransferase gene *S. argillaceus* M7W 1 can be mutated prior to or after the mutation of the mtmW gene *S. argillaceus* M7W 1.

Mithramycin SK has a molecular formula of $C_{51}H_{74}O_{23}$ and a molecular weight of 1054.4. The $^1$H-NMR and $^{13}$C-NMR data are provide in Table 1 and based on the following labeling scheme:

TABLE 1

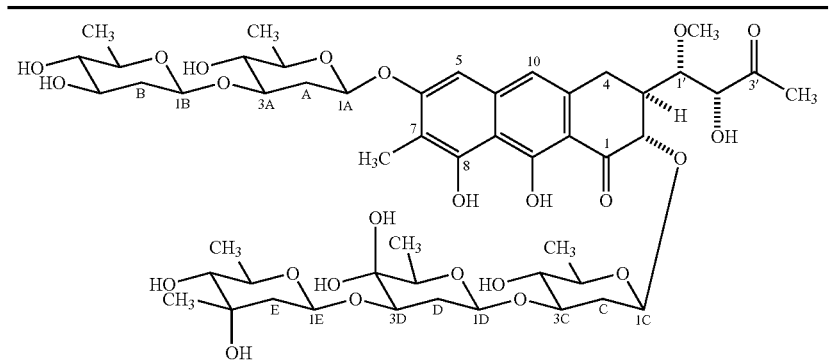

$^1$H-NMR (acetone-$d_6$, 400 MHz) and $^{13}$C-NMR (acetone-$d_6$, 100 MHz) Data for Mithramycin-SK

| Position | $^1$H δ (ppm) | Multiplicity, J (Hz) | $^{13}$C δ (ppm) | HMBC |
|---|---|---|---|---|
| 1 | — | — | 203.5 | |
| 2 | 4.7 | d (11.5) | 78.18 | 1C, 3, $4_a$, $4_e$, 1' |
| 3 | 2.48 | overlap | 43.71 | 2, 4a, 4e, 1', 2' |
| $4_a$ | 3.15 | dd (16, 3) | 28.3 | 2, 10, 1', 2' |
| $4_e$ | 2.99 | overlap | 28.3 | |
| 4a | — | — | 136.9 | |
| 5 | 6.87 | s | 101.7 | |
| 6 | — | — | 159.9 | |
| 7 | — | — | 111.0 | |
| 7-CH$_3$ | 2.15 | s | 7.91 | |
| 8 | — | — | 156.2 | |
| 8a | — | — | 108.0 | |
| 9 | — | — | 165.3 | |
| 9a | — | — | 108.5 | |
| 10 | 6.89 | s | 117.0 | |
| 10a | — | — | 139.1 | |
| 1' | 4.25 | dd (3.4, 1.5) | 79.28 | 1'-OCH$_3$ |
| 1 | — | — | 203.5 | |

TABLE 1-continued

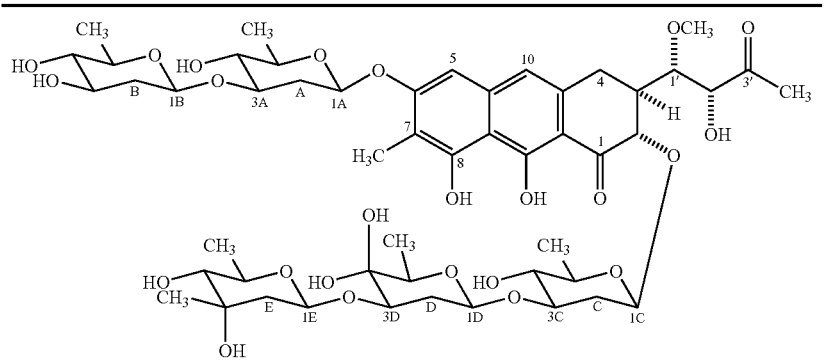

$^1$H-NMR (acetone-$d_6$, 400 MHz) and $^{13}$C-NMR (acetone-$d_6$, 100 MHz) Data for Mithramycin-SK

| Position | $^1$H δ (ppm) | Multiplicity, J (Hz) | $^{13}$C δ (ppm) | HMBC |
|---|---|---|---|---|
| 1'-OCH$_3$ | 3.55 | S | 59.99 | 1' |
| 2' | 4.32 | d(3.4) | 79.46 | 2, 1'-OCH$_3$, 4' |
| 3' | — | — | 209.9 | 1', 2' |
| 4' (CH$_3$) | 2.35 | S | 26.26 | 1-J coupling |
| 1A | 5.37 | dd (10, 2) | 97.0 | |
| 2A$_a$ | 1.86 | ddd (12, 12, 10) | 37.5 | |
| 2A$_c$ | 2.48 | overlap | 37.5 | |
| 3A | 3.78 | ddd (12, 9, 5) | 81.30 | |
| 4A | 3.09 | dd (9, 9) | 75.40 | |
| 5A | 3.55 | overlap | 72.6 | |
| 6A (CH$_3$) | 1.34 | d (6) | 17.97 | |
| 1B | 4.75 | dd (10, 2) | 99.9 | |
| 2B$_a$ | 1.59 | ddd (12, 12, 10) | 39.97 | |
| 2B$_e$ | 2.20 | ddd (12, 5, 2) | 39.97 | |
| 3B | 3.58 | overlap | 71.38 | |
| 4B | 3.01 | dd (9, 9) | 77.55 | |
| 5B | 3.41 | dq (9, 6) | 72.6 | |
| 6B (CH$_3$) | 1.34 | d (6) | 17.65 | |
| 1C | 5.14 | dd (10, 2) | 100.8 | |
| 2C$_a$ | 1.62 | ddd (12, 12, 10) | 37.92 | |
| 2C$_e$ | 2.51 | ddd (12, 5, 2) | 37.92 | |
| 3C | 3.68 | overlap | 81.76 | |
| 4C | 3.05 | dd (9, 9) | 75.69 | |
| 5C | 3.33 | dq (9, 6) | 72.6 | |
| 6C (CH$_3$) | 1.34 | d (6) | 17.93 | |
| 1D | 4.70 | dd (10, 2) | 100.3 | |
| 2D$_a$ | 1.8 | Ddd (12, 12, 10) | 32.51 | |
| 2D$_e$ | 1.95 | ddd (12, 5, 2) | 32.51 | |
| 3D | 3.88 | ddd (12, 5, 3) | 77.32 | |
| 4D | 3.72 | bs | 68.87 | |
| 5D | 3.7 | overlap | 71.0 | |
| 6D (CH$_3$) | 1.34 | d (6) | 16.54 | |
| 1E | 4.98 | dd (9.5, 2) | 97.9 | |
| 2E$_a$ | 1.56 | dd (13, 9.5) | 44.34 | |
| 2E$_e$ | 1.90 | dd (13.5, 2) | 44.34 | |
| 1 | — | — | 203.5 | |
| 3E | — | — | 70.7 | |
| 3E-CH$_3$ | 1.22 | s | 27.02 | |
| 4E | 2.99 | d (9) | 76.81 | |
| 5E | 3.65 | overlap | 71.0 | |
| 6E (CH$_3$) | 1.22 | d (6) | 26.26 | |

Demycarosyl-mithramycin SK has a molecular formula of $C_{44}H_{62}O_{20}$ and a molecular weight of 933.4, and has the following $^1$H-NMR and $^{13}$C-NMR data: $^1$H-NMR (500 MHz, acetone-$d_6$, δ): 1.33 (d, 12H, J=6 Hz, 6A-H3, 6B-Ha, 6C—H$_3$, and 6D-H$_3$), 1.58 (ddd, 1H, J=12, 12, 10 Hz. 2B—H.), 1.62 (ddd, 1H, J=12, 12, 10 Hz, 2C—H.), 1.76 (ddd, 1H, J=12, 12,10 Hz,2D—H$_a$), 1.90 (ddd, 1H, J=12, 12, 10Hz, 2A-H$_a$), 1.95 (ddd, 1H, J=12, 5, 2 Hz, 2D-H$_e$), 2.17 (s, 3H, 7-CH$_3$), 2.21 (ddd, 1H, J=12, 5, 2 Hz, 2B—H$_e$), 2.34 (s, 3H, 4'-H$_3$), 2.47 (overlap, 1H, 3-H), 2.49 (overlap, 1H, 2A-H$_e$), 2.51 (overlap, 1H, 2C—H$_e$), 2.99 (dd, 1H, J=9,9 Hz, 4B—H), 3.01 (overlap, 2H, 4-H$_e$), 3.01 (dd, 1H, J=9, 9 Hz, 4C—H), 3.08 (dd, 1H, J=9, 9 Hz, 4A-H), 3.19 (dd, 1H, J=16, 3 Hz, 4-H$_a$), 3.35 (dq, 1H, J=9, 6 Hz, 5C—H), 3.38 (dq, 1H, J=9, 6 Hz, 5B—H), 3.54 (bs, 1H, 4D-H), 3.56 (s, 3H, 1'-OCH$_3$), 3.56 (overlap, 1H, 5A-H), 3.58 (overlap, 1H, 3B—H), 3.69 (overlap, 1H, 3C—H),3.71 (bq, 1H, J=6 Hz, 5D-H), 3.78 (ddd, 1H, J=12, 9, 5 Hz, 3A-H), 3.80 (ddd, 1H, J=12, 5, 3 Hz, 3D-H), 4.24 (dd, 1H, J=3.4, 1.5 Hz, 1'-H), 4.31 (d, 1H, J=3.4 Hz, 2'-H), 4.69 (dd, 1H, J=10, 2 Hz, 1D-H), 4.77 (d, 1H, J=11.5 Hz, 2-H), 4.77 (dd, 1H, J=10, 2 Hz, 1B—H), 5.14 (dd, 1H, J=10, 2 Hz, 1C—H), 5.43 (dd, 1H, J=10, 2 Hz, 1A-H), 6.94 (s, 2H, 5-H, and 10-H). $^{13}$C-NMR (125.7 MHz, acetone-d$_6$, δ): 7.9 (7-CH$_3$), 16.5 (C-6D), 17.6 (C-6B), 17.9 (C-6C and C-6A), 26.2 (C-4'), 28.3 (C-4), 35.2 (C-2D), 37.5 (C-2A), 37.9 (C-2C), 40.0 (C-2B), 43.8 (C-3), 60.0 (1'-OCH$_3$), 68.9 (C-3D), 70.2 (C-4D), 71.3 (C-5D), 72.7 (C-5A and C-5C), 75.4 (C-4A), 75.7 (C-4C), 77.5 (C-4B), 78.1 (C-2), 79.30 (C-1'), 79.5 (C-2'), 81.3 (C-3A), 81.7 (C-3C), 97.1 (C-1A), 99.9 (C-1B), 100.4 (C-1D), 100.8 (C-1C), 101.7 (C-5), 108.0 (C-8a), 108.6 (C-9a), 111.1 (C-7), 117.1 (C-10), 137.0 (C-4a), 139.1 (C-10a), 156.1 (C-8), 160.0 (C-6), 165.4 (C-9), 203.6 (C-1) and 209.8 (C-3').

Mithramycin SA has a molecular formula of C$_{49}$H$_{70}$O$_{23}$ and a molecular weight of 1049.4, and has the $^1$H-NMR and $^{13}$C-NMR data: $^1$H-NMR (400 MHz, pyridine-d5, δ): 1.50 (s, 3H, 3E-CH$_3$), 1.52 (d, 3H, J=6.5 Hz, 6E-H$_3$), 1.62 (d, 9H, J=6.0 Hz, 6A-H$_3$, 6C—H$_3$, and 6D-H$_3$), 1.68 (d, 3H, J=6.0 Hz, 6B—H$_3$), 1.77 (bt, 2H, J=10.0 Hz, 2E-H$_a$, and 2B—H$_a$), 1.92 (bdd, 1H, J=12, 9 Hz, 2C—H$_a$), 2.02 (bdd, 1H, J=12, 11 Hz, 2D-H$_a$), 2.08-2.22 (overlap, 2H, 2A-H$_a$, and 2D-H$_a$, and 2D-H$_e$), 2.28 (dd, 1H, J=9, 2 Hz, 2E-H$_e$), 2.38 (bd, 1H, J=10 Hz, 2A-H$_e$), 2.47 (s, 3H, 7-CH$_3$), 2.54 (m, 1H, 2C—H$_e$), 2.79 (m, 1H, 2B-Hc), 2.93(m, 1H, 4-H$_e$), 3.11 (bt, 1H, J=15.2 Hz, 4-H$_a$) 3.14(bt, 1H, J=11 Hz, 3-H), 3.36 (d, W,J=9 Hz, 4E-H), 3.49-3.72 (overlap, 4H, 3A-H, 3B—H, 3C—H, and 5A-H), 3.55 (dd, 1H, 9, 8.5 Hz, 4C—H), 3.62 (s, 3H, 1'-OCH$_3$), 3.84 (bdd, 1H, J=12.0, 4.5 Hz, 3D-H), 3.93-4.02 (overlap, 4H, 4A-H, 4B—H, 4D-H, 5C—H, and 5D-H), 3.98 (dq, 1H, J=10.0, 6.0 Hz, 5E-H), 4.29 (dq, 1H, J=10.0, 6.0 Hz, 5B—H), 4.76 (bd, 1H, J=10 Hz, 1D-H), 4.86 (d, 1H, J=1.5 Hz, 1'-H), 4.92 (d, 1H, J=11 Hz, 2-H), 5.00 (dd, 1H, J=10, 2 Hz 1B—H), 5.41 (dd, 1H, J=10, 2 Hz, 1C—H), 5.53 (dd, 1H, J=10, 2 Hz, 1E-H), 5.61 (dd, J=10, 2 Hz, 1A-H), 6.61 (s, 1H, 10-H), and 7.01 (s, 1H, 5-H). $^{13}$C-NMR (75.4 MHz. methanol-d$_4$, δ): 7.1 (7-CH$_3$),15.9 (C-6D), 17.1 (C-6B), 17.3 (C-6C), 17.4 (C-6A), 18.0 (C-6E), 26.3 (3E-CH$_3$), 29.7 (C-4), 32.3 (C-2D), 37.1 (C-2A), 37.5 (C-2C), 39.7 (C-2B), 44.6 (C-2E and C-3), 59.6 (1'-OCH$_3$), 68.7 (C-4D), 70.7 (C-3E and C-5E), 70.9 (C-3B and C-5D), 72.5 (C-5C and C-5B), 72.9 (C-5A), 75.1 (C-4A), 75.7 (C-4C), 76.2 (C-3D), 76.8 (C-4E), 77.0 (C-2 and C-4B), 79.5 (C-3A), 81.5 (C-3C), 82.2 (C-1'), 97.5 (C-1A) 97.6 (C-1E), 98.8 (C-1B and C-1D), 100.0 (C-1C), 100.1 (C-5), 108.0 (C-8a), 108.6 (C-9a), 111.7 (C-7), 117.2 (C-10), 138.5 (C-4a), 138.7 (C-10a), 159.2 (C-6), 160.5 (C-8), 165.0 (C-9), 176.8 (C-2') and 198.4 (C-1).

Production and Isolation of Mithramycin SDK

A seed culture was prepared using TSB inoculated with spores of the S. argillaceus M7W1 mutant and incubated in an orbital shaker for 24 hours at 30° C. and 195 rpm. This seed culture was used to inoculate (at 2.5%, v/v) twenty 250 ml Erlenmeyer flasks, each containing 100 ml of modified R5 media for five days. The cultured media was centrifuged at 4,000 rpm for 30 minutes and the supernatants passed through a reverse phase column (4.5×10 cm) with pressure followed by washing the column with acetonitrile:water (5:95). Three fractions were collected eluting with ACN:water mixtures and increasing the ACN partition: fraction 1 (20% ACN) contains mithramycin-SA, fraction 2 (25% ACN) contains mithramycin-SK, and fraction 3 (31% acetonitrile) contains mithramycin-SDK. Fraction three (F3) was further purified by a reverse phase column (1.5×15 cm, ACN:water 33:67), yielding 28.4 mg mithramycin-SDK.

Mithramycin-SDK has a molecular formula of C$_{51}$H$_{72}$O$_{23}$ and a molecular weight of 1053.1. The $^1$H-NMR and $^{13}$C-NMR data are provide in Table 2 and based on the same labeling scheme as for Mithramycin-SK:

TABLE 2

$^1$H-NMR (pyridine-d$_5$, 400 MHz) and $^{13}$C-NMR (pyridine-d$_5$, 100 MHz) Data for Mithramycin SDK

| Position | δ $^1$H (ppm) | Multiplicity J (Hz) | δ $^{13}$C (ppm) | Important $^3$J HMBC |
|---|---|---|---|---|
| Aglycon | | | | |
| 1 | — | — | 204.3 | — |
| 2 | 4.87 | d (12) | 78.0 | 1C, 4, 9a |
| 3 | 3.09 | dddd (12, 12, 3, 1) | 43.6 | 1, 4a, 2' |
| 4$_{ax}$ | 3.27 | (br dd, 16, 12) | 28.4 | 2, 10, 9a, 1' |
| 4$_{eq}$ | 2.85 | dd (16, 3) | | 2, 9a, 1' |
| 4a | — | — | 136.6 | — |
| 5 | 7.09 | s | 100.9 | 7, 8a, 10 |
| 6 | — | — | 160.3 | — |
| 7 | — | — | 111.5 | — |
| 7-CH$_3$ | 2.44 | s | 9.4 | 6, 8 |
| 8 | — | — | 157.4 | — |
| 8a | — | — | 109.6 | — |
| 9 | — | — | 166.8 | — |
| 9a | — | — | 109.6 | — |
| 10 | 6.70 | br. S | 117.4 | 5, 8a, 9a, 4 |
| 10a | — | — | 139.5 | — |
| 1' | 5.49 | d (1) | 83.5 | 2, 4, —OCH$_3$, |
| 1'-OCH$_3$ | 3.72 | s | 59.7 | 1' |
| 2' | — | — | 198.6 | — |
| 3' | — | — | 199.5 | — |
| 4' | 2.42 | s | 26.4 | 2' |
| Sugar A (β-D-olivose) | | | | |
| 1A | 5.62 | dd (10, 2) | 98.4 | 6 |
| 2A$_{ax}$ | 2.16 | ddd (12, 12, 10) | 37.4 | |
| 2A$_{eq}$ | 2.51 | m (overlap) | | |
| 3A | 4.54 | ddd (12, 9, 5) | 81.3 | 1B |
| 4A | 3.43 | dd (9, 9) | 75.4 | |
| 5A | 3.55 | m (overlap) | 72.6 | |
| 6A | 1.56 | d (6) | 18.0 | |
| Sugar B (β-D-olivose) | | | | |
| 1B | 5.56 | dd (10, 2) | 100.2 | 3A |
| 2B$_{ax}$ | 2.04 | ddd (12, 12, 10) | 40.0 | |
| 2B$_{eq}$ | 2.46 | m (overlap) | | |
| 3B | 4.44 | m (overlap) | 71.4 | |
| 4B | 3.33 | dd (9, 9) | 77.6 | |
| 5B | 3.41 | dq (9, 6) | 72.6 | |
| 6B | 1.45 | d (6) | 17.7 | |
| Sugar C (β-D-olivose) | | | | |
| 1C | 5.39 | dd (10, 2) | 100.8 | 2 |
| 2C$_{ax}$ | 1.80 | ddd (12, 12, 10) | 37.9 | |
| 2C$_{eq}$ | 2.95 | ddd (12, 5, 2) | | |
| 3C | 4.09 | m (overlap) | 81.8 | 1D |
| 4C | 3.47 | dd (9, 9) | 75.7 | |
| 5C | 3.65 | dq (9, 6) | 72.6 | |
| 6C | 1.38 | d (6) | 17.9 | |
| Sugar D (β-D-oliose) | | | | |
| 1D | 4.74 | dd (10, 2) | 100.3 | 3C |
| 2D$_{ax}$ | 1.79 | ddd (12, 12, 10) | 32.5 | |
| 2D$_{eq}$ | 2.43 | ddd (12, 5, 2) | | |
| 3D | 3.98 | ddd (12, 5, 3) | 77.3 | 1E |
| 4D | 3.53 | br. S | 68.9 | |
| 5D | 3.63 | m (overlap) | 71.0 | |
| 6D | 1.39 | d (6) | 16.5 | |
| Sugar E (β-D-macarose) | | | | |
| 1E | 5.34 | dd (9.5, 2) | 97.9 | 3D |
| 2E$_{ax}$ | 2.34 | dd (13, 9.5) | 44.3 | |
| 2E$_{eq}$ | 2.46 | dd (13, 2) | | |
| 3E | — | — | 70.7 | |
| 3E-CH$_3$ | 1.93 | s | 27.0 | 2E, 4E |
| 4E | 3.09 | d (9) | 76.8 | |
| 5E | 4.65 | m (overlap) | 71.0 | |
| 6E | 1.57 | d (6) | 17.7 | |

In FIG. 3, mithramycin-SA structure 4 gives indirect evidence for the labile MTM structure 5, because its formation from 5 is possible through the attack of water at the carbonyl adjacent to the methoxy group, followed by retro-aldol cleavage to yield mithramycin-SA structure 4 and hydroxyacetone. To prove the excision of carbon 3', two feeding experiments using [1-13C]-acetate and [1,2-13C2]-acetate were performed.

Figure 5:
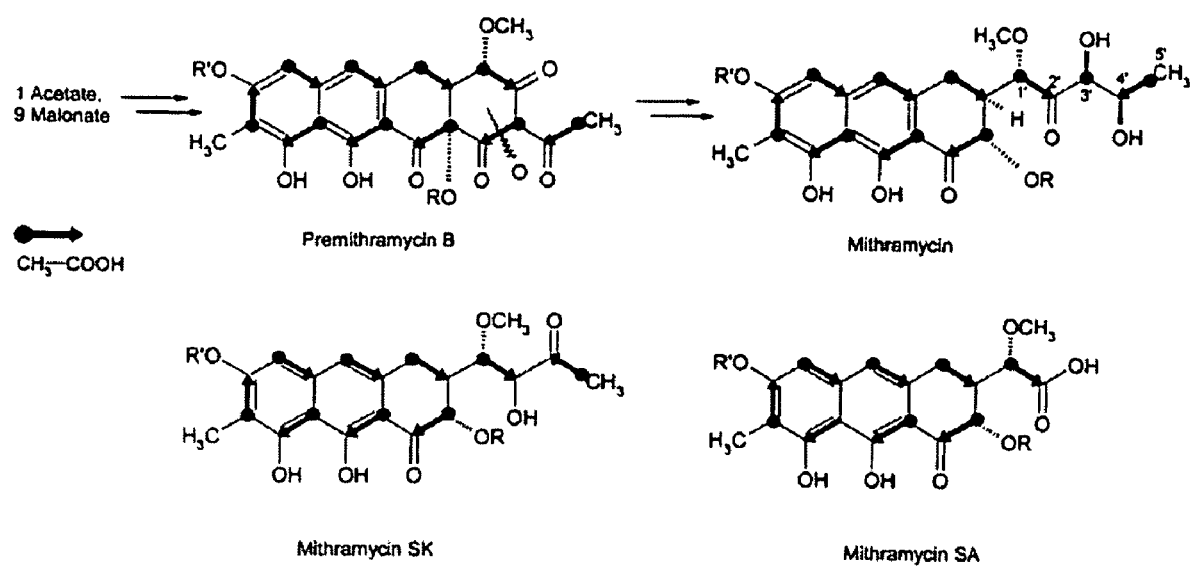
FIG. 5 shows a comparison of the rearrangement of the tetracyclic rings in forming MTM, mithramycin-SK and mithramycin-SA.

FIG. 5 shows the results of incorporation experiments with [1-$^{13}$C]-acetate and [1,2-$^{13}$C$_2$]-acetate on the mithramycin-SK and mithramycin-SA produced from *S. argillaecus* M7W1, compared to the normal incorporation pattern found in mithramycin. In FIG. 5, R and R' are the deoxysaccharide chains shown in formulas (III) and (V). The comparison reveals that the former mithramycin carbon carbon 3' and carbons 3', 4' and 5' respectively, were excised during the formation of mithramycin-SK and mithramycin-SA, respectively. It is believed that the β-dicarbonyl constellation triggers a Favorskii-like rearrangement, for which an 1,2-acyl shift induced by deprotonation of the central alcohol can be envisaged, followed by the addition of water on the resulting aldehyde and a consequent departure of formic acid.

The oxidative rearrangement during the biosynthesis of MTM leads to an acetate incorporation pattern as shown in FIG. 5, wherein carbons 4' and 5' of the carbon 3 side chain stem from the starter unit, whereas carbons 1', 2', and 3' were once the end of the polyketide chain. If carbon 3' is lost, two intact acetate units facing each other from opposite directions should result. The results, also shown in FIG. 5, are consistent with these expectations and, thus, prove the loss of carbon 3'.

Biological Activity

The mithramycin SK has antitumor activity substantially higher than that of MTM and is particularly active against melanoma, leukemia and CNS cancer cells. Moreover, initial in vitro anticancer assays, pursued by the NCI (National Cancer Institute, Bethesda, Md.) against 60 human cancer cell lines, as well as an in vitro toxicity assay generated promising results in that mithramycin-SK showed an up to two orders of magnitude better antitumor activity and a two orders of magnitude lesser toxicity than the parent compound MTM itself.

Table 3 shows IC$_{50}$ values (μg/kg) of active extracts of the cancer cells. The experiment was performed by Biotecon, Berlin. It measures the uptake of sulforhodamin B (SRB), which is dependent on the cellular protein quantities, and can be performed in 96-well microtiter plates according to the protocol published by Boyd et al. (NCI). The SRB assay is a rapid and sensitive method to measure drug-induced cytotoxicity. Briefly, cells will be incubated with and without drug for 72 hours (drugs will be added after 24 hours), fixed with TCA (trichloroacetic acid), and stained for 30 minutes using a 0.4% (w/v) SRB solution in 1 acetic acid. Cultures will then be rinsed with 1% acetic acid, residual wash solution will be removed and air-dried. Bound dye will be solubilized with 10 mM unbuffered Tris base (pH 10.5) for 5 min., and the optical density (OD) will be measured with a microtiter plate reader at 564 nm. (Skehan, P. et al., "New calorimetric cytotoxicity assay for anticancer-drug screening," *Journal of the National Cancer Institute*, 1990. 82(13): p. 1107-1112). The data indicate that mithramycin-SK was much more effective in reducing the growth of cancer cells in lung, breast and CNS cells when compared to other anti-cancer compounds at the same concentration.

TABLE 3

Proliferation Inhibition Assays - Percent Growth in 48 Hours

| Mithramycin Compound | Concentration (molar) | Lung (NCI-H460) | Breast (MCF-7) | CNS (SF-268) |
|---|---|---|---|---|
| Premithramycin A$_1$ | 1 × 10$^{-4.6}$ | 68 | not tested | 93 |
| Premithramycin B | 1 × 10$^{-5}$ | >100 | >100 | >100 |
| Mithramycin | 1 × 10$^{-5}$ | 12 | 12 | not tested |
| Mithramycin-SK | 1 × 10$^{-5}$ | 0.1 | 0.2 | 1 |
| Demycarosyl-Mithramycin-SK | 1 × 10$^{-5}$ | 5 | 22 | 47 |

The cytotoxicity of Mithramycin-SK and demycarosyl-mithramycin-SK were assessed in a panel of 60 cell lines using a sulforhodamine B assay. It is active against a variety of tumor cell lines in the concentration range of 10$^{-5}$ to 10$^{-8}$ molar. Cell lines were inoculated into a series of 96-well microliter plates with varying seeding densities depending on the growth characteristics of the particular cell lines. Following a 24 hour drug-free incubation, mithramycin-SK was added routinely at five 10-fold dilutions with maximum concentration of 10.4 M. After 48 hours of drug exposure, the change in protein stain optical density allowed the inhibition of cell growth to be analyzed.

Mithramycin-SK and demycarosyl-mithramycin-SK were also tested in a neutral red toxicity assay. In this experiment, non-tumorous mouse fibroblast cells were used (NIH 3T3). After 24 hours of incubation, Mithramycin-SK showed no toxicity even at 200 μg/mL, while the revealing antiproliferative activity in concentrations <1 μg/mL.

Compilation of the average log(GI$_{50}$) values showed that both compounds were active, with mithramycin-SK (activity up to 9 times higher than that of MTM) being much more active than demycarosyl-mithramycin-SK (ca.25 times less active than MTM). Mithramycin-SK was particularly active against melanoma, leukemia, and CNS cancer cells (log (GI50) values of −7.64, −7.59, and −7.61, respectively). Given the increased activity observed for mithramycin-SK, a neutral red uptake analysis of squamous, melanoma, lung, and breast carcinomas was performed, which not only confirmed the increased activity of mithramycin-SK as compared to MTM, but also showed an even more pronounced improvement of activity (up to ca. 90 times better). In addition, toxicity assays using this same process and mouse 3T3 fibroblast (nontumor) cells showed that 2, with an IC$_{50}$ value of 1.96× 10$^{-5}$ M, is more than 1500-fold less toxic than MTM (IC$_{50}$ values ranging from 1.29×10$^{-8}$ to 3.45×10$^{-9}$ M). Thus, mithramycin-SK displays a significantly improved therapeutic index, up to 4 orders of magnitude better when compared to its parent compound, MTM. The results are shown in Table 4.

TABLE 4

Antitumor Analysis Comparing Mithramycin (1), Mithramycin SK (2), and Demycarosyl-Mithramycin-SK (3).

| | | | Composition with 2 | | Composition with 3 | |
|---|---|---|---|---|---|---|
| Type of Cancer | 1 | 2 | Δ$_{1-2}$ | AIF[a] | 3 | Δ$_{1-3}$ | AIF |
| | Average Log(GI$_{50}$) Values from Sulforhodamine B Assay | | | | | | |
| Leukemia (5)[b] | −6.65 | −7.59 | 0.94 | 8.7 | −5.55 | −1.10 | 0.08 |
| NSCLC (8)[b] | −6.73 | −7.37 | 0.64 | 4.4 | −5.30 | −1.43 | 0.04 |
| Colon (7)[b] | −6.65 | −7.32 | 0.67 | 4.7 | −5.35 | −1.30 | 0.05 |
| CNS (5)[b] | −6.78 | −7.61 | 0.83 | 6.8 | −5.30 | −1.48 | 0.03 |

TABLE 4-continued

Antitumor Analysis Comparing Mithramycin (1), Mithramycin SK (2), and Demycarosyl-Mithramycin-SK (3).

|  | | | Composition with 2 | | Composition with 3 | |
|---|---|---|---|---|---|---|
| Type of Cancer | 1 | 2 | $\Delta_{1-2}$ | AIF[a] | 3 | $\Delta_{1-3}$ | AIF |
| Melanoma (8)[b] | −6.72 | −7.64 | 0.92 | 8.3 | −5.37 | −1.35 | 0.04 |
| Ovarian (6)[b] | −6.60 | −7.53 | 0.93 | 8.5 | −5.23 | −1.37 | 0.04 |
| Renal (8)[b] | −6.73 | −7.29 | 0.56 | 3.6 | −5.14 | −1.59 | 0.03 |
| Prostrate (2)[b] | −6.90 | −7.48 | 0.58 | 3.8 | −5.25 | −1.65 | 0.02 |
| Breast (8)[b] | −6.59 | −5.89 | −0.70 | 0.2 | −5.15 | −1.44 | 0.04 |
| Average Log(GI$_{50}$) Values from Neutral Red Assay | | | | | | | |
| Squamous carcinoma | −5.04 | −5.99 | 0.95 | 8.9 | | | |
| Melanoma | −5.05 | −6.25 | 1.20 | 15.8 | | | |
| Lung carcinoma | −4.92 | −6.88 | 1.96 | 91.2 | | | |
| Breast carcinoma | −4.95 | −6.74 | 1.79 | 61.6 | | | |

[a]Activity improvement factor. This factor is equal to $10^{\Delta_{1-x}}$, where x is the identifying value for compound 2 or 3. An AIF of 1.0 corresponds to no difference in activity.
[b]The number in parenthesis is the number of cell lines tested in each family.

The data in Table 4 shows that mithramycin-SK (compound 2) exhibits an activity that is up to 90 times higher than MTM (compound 1).

Therapeutic Administration of the Mithramycin Derivatives

The dosages or amounts of the compounds of the invention are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration may be varied. Doses and dosing regimens used form Mithramycin provide guidance for dose and dosing regimens for Mithramycin SK (see for example Trask and Sonhami, "Effect of Mithramycin on Widespread Painful Bone Metastases in Cancer of the Breast," Cancer Treat. Rep., 63(11-12): 1835-1838 (1979); and Conrad et al., "Mithramycin in the Treatment of Systemic Mastocytosis," Ann. Intern. Med., 83(5): 659-660 (1975)). For example, a single or multiple dose can be administered. In one embodiment, the dosages can be in ranges from 0.1 to 100 mg/kg, 0.1 to 90 mg/kg, 0.1 to 80 mg/kg, 0.1 to 70 mg/kg, 0.1 to 50mg/kg, 0.1 to 20 mg/kg, 0.1 to 10 mg/kg, 0.1 to 5 mg/kg or 0.1 to 1 mg/kg. In another embodiment, the compounds of the invention can also be administered for 5 days with a daily dose of 0.12 mg/kg. In yet another embodiment, a single dose of 1.0 mg/kg to 10 mg/kg can be administered.

Any of the compounds of the invention can be used therapeutically in combination with a pharmaceutically acceptable carrier. Pharmaceutical carriers are known to those skilled in the art. These most typically would be standard carriers for administration of compositions to humans and non-humans, including solutions such as sterile water, saline, and buffered solutions at physiological pH. Other compounds will be administered according to standard procedures used by those skilled in the art.

Any of the compounds of the invention intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The compounds of the invention may be administered to the subject in a number of ways depending on whether local or systemic treatment is desired, and on the area to be treated. Thus, for example, a compound of the present invention can be administered as an ophthalmic solution and/or ointment to the surface of the eye. Moreover, a compound can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Preparations for parenteral administration include sterile aqueous or non-aqueous solutions, suspensions, and emulsions which may also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration may include powders or granules, suspensions or solutions in water or non-aqueous media, capsules, sachets, or tablets. Thickeners, flavorings, diluents, emulsifiers, dispersing aids or binders may be desirable.

In one embodiment, the compounds of the invention are administered to a subject comprising a human or an animal including, but not limited to, a mouse, dog, cat, horse, bovine or bovine and the like, that is in need of alleviation or amelioration from a recognized medical condition.

The present invention also provides a method of treating Paget's Disease in a subject diagnosed with Paget's Disease, comprising administering to the subject an effective amount of a compound of the invention, whereby the compound treats the Paget's Disease in the subject. The subject can be a mammal, preferably a human, and the compound is administered parenterally.

Further provided by the present invention is a method of treating hypercalcemia in a subject diagnosed with hypercalcemia, comprising administering to the subject an effective amount of a compound of the invention in a pharmaceutically acceptable carrier, whereby the compound treats hypercalcemia in the subject. The subject can be a mammal, preferably a human, and the compound is administered parenterally.

The present invention also provides a method of providing neuroprotection in subject diagnosed with neurological diseases, the method comprising the step of administering to the subject an effective amount of a compound of the invention in a pharmaceutically acceptable carrier, whereby the compound provides neuroprotection in the subject. The subject can be a mammal, preferably a human, and the compound is administered parenterally.

The present invention also provides a method of providing neuroprotection in subject diagnosed with neurological diseases, the method comprising the step of administering to the subject an effective amount of a compound of the invention in a pharmaceutically acceptable carrier, whereby the compound provides neuroprotection in the subject. The subject can be a mammal, preferably a human, and the compound is administered parenterally.

The compounds of the invention can be useful as a biochemical tool. For example, the compounds can be useful to block the c-Src (and other Sp1-dependent enzymes) expression in osteoclast or other cells.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

This invention is not limited to specific synthetic methods, specific compositions, or to particular formulations, as such may, of course, vary. It is also to be understood that the terminology used herein is for the purpose of describing particular embodiments only and is not intended to be limiting.

SEQUENCE LISTING

```
<160> NUMBER OF SEQ ID NOS: 1

<210> SEQ ID NO 1
<211> LENGTH: 5975
<212> TYPE: DNA
<213> ORGANISM: Streptomyces argillaceus

<400> SEQUENCE: 1
ggatcctcgt ccgtctcgac caccaggtag cggctcagcg cccggtagaa acggccgccc      60
tcctcggact gcacggcgtc gtagaggatc tgctccggcc gggccgcgag cacctggtcc     120
aggaacctgg gccgctgttc gggggggaga tgagcgtggt cgtcggggac gcactggacg     180
gtcggggcca gctcgatgag gtcgacgtag cccggttccg ggtgggcgcg cgccaggacg     240
tggaggacgc cgtcgatccg cttggccagg aacgccacca ccccggtgcc gcgcgggctg     300
agcagcggct gggtccaccc cttgacttcg cggttgccgg cctccacaga cacggcgacg     360
atcgcgaagt gccgtccact ggtgtggcgt atctcgtccg tgtcgcggac ccagccgtcc     420
acggaggtca gcgggacgag ctgcgcggcg acctcgctgc gcgccctgag cccgttgaac     480
cagcgcagca gctcgggcag ggtgtgcgcg gcgggggcct gcgcggacag ggaggcggtc     540
agggcggcca cggccgcccc gcgggaaccg tcggtcgtga ctccctcgag ggaaccgtcc     600
ggcggggcga cggggaggca ggccaggacc gtccgagtgt ccatgttgac caggtccggg     660
acgccgagca gccggcggac ctgaccgagg gtcagccagc ggtagtcctc gtgctcgggc     720
acgtcgccga cggcctcgac gacgagattg cggttgcgtt tgcggaagaa ccaggaaccg     780
tgctcggact ggagcacgtc gaccagcggc cggcccttgc cggggtccgt gaagtactcc     840
aggtaccgca cggcgctgcc ctcgtgcacg cccgtgtagt tgctgcgggt ggcctgcacc     900
gtgggcgaca actggagtcc ctcggcgttg ccgggctcgg ccttcgcctg catcaggcag     960
tgcaggacac cgtcgaactc cttgaccagg atgccgagga aacccacttc cggctggtgc    1020
atgatcggct gggaccagga gacggggtcc gggccctcgg agcgagcccg cagcccttcg    1080
acggtgaaga agcggccgct gtcgtgcgcc agattccgg tgaccgggtg gaagccccag    1140
cgctggagct cggcgaaggg gatgcgcctc acgtccatcc ggatggcctt gcggcgctcc    1200
tcgaaccagt cgtggacacc acccagggac agcagtccgc tgtcggccgc cgccgattcg    1260
```

```
gcgatgcgcc tcagatccgg cgcgtcgagg ccgtccgggg ggaccgctgg atgctttctg    1320
ctcatgatcg cttgagtcat ggatgtctct cccatcgcag gcatcggcag cgcgctcggg    1380
ccaccgtcgg cacccaggct ggagtcgcgc tcgaggcccg gtcggtccgg accgggcgga    1440
cggcggttcc gtcagggctc gagccgcctt cgatcagggc ggccgaacgt ggtcgccgtg    1500
gagttccgaa gccttggccg aagtggcctt tcagtgagtg agatcgtgta cggcaacctg    1560
ctgtacccgc aggacgacac ccccgacgag gtggttctct cctcgatcag agcggccctt    1620
gacgccgggg tgacgacctt cgacaccgcg gacgtctacg gcatgttccg ctccgagagc    1680
ctgctgggcg gggcactggc cggcacgccc cgcgaagagc tggtgctgtg caccaaggtg    1740
gggatgccga ccgggttcgg gcccaacgga cgggggctgt cgaggaaaca cgtcatggag    1800
tccgtcgacg gctcgctgcg ccgtctgcgc gtcgaccaca tcgacgtcta caccgcgcac    1860
cgctacgacc cggcgactcc gctggaggag ctgatgtgga ccttctccga cctggtacgg    1920
gccgggaaga tcctctacgt cggcatgtcg gaatggcccg tggagcggat cgccgaggcg    1980
gccgggatag gtgcgcggct cggtgtgccg gtgatctgtc acatgccccg ctactcgatg    2040
ctgtggcggg cgccggaggc cgaggtgatc cccgcctgcc gtgacctggg catcggccag    2100
atcgggagct cgaattcgaa gcttctgcag ctcacggtaa ctgatgccgt atttgcagta    2160
ccagcgtacg gcccacagaa tgatgtcacg ctgaaaatgc cggcctttga atgggttcat    2220
gtgcagctcc atcagcaaaa ggggatgata agtttatcac caccgactat ttgcaacagt    2280
gccgttgatc gtgctatgat cgactgatgt catcagcggt ggagtgcaat gtcgtgcaat    2340
acgaatggcg aaaagccgag ctcatcggtc agcttctcaa ccttggggtt accccccggcg    2400 gtgtgctgct ggtccacagc tccttccgta gcgtccggcc cctcgaagat gggccacttg    2460
gactgatcga ggccctgcgt gctgcgctgg gtccgggagg gacgctcgtc atgccctcgt    2520
ggtcaggtct ggacgacgag ccgttcgatc ctgccacgtc gcccgttaca ccggaccttg    2580
gagttgtctc tgacacattc tggcgcctgc caaatgtaaa gcgcagcgcc catccatttg    2640
cctttgcggc agcggggcca caggcagagc agatcatctc tgatccattg cccctgccac    2700
ctcactcgcc tgcaagcccg gtcgcccgtg tccatgaact cgatgggcag gtacttctcc    2760
tcggcgtggg acacgatgcc aacacgacgc tgcatcttgc cgagttgatg gcaaaggttc    2820
cctatggggt gccgagacac tgcaccattc ttcaggatgg caagttggta cgcgtcgatt    2880
atctcgagaa tgaccactgc tgtgagcgct ttgccttggc ggacaggtgg ctcaaggaga    2940
agagccttca gaaggaaggt ccagtcggtc atgcctttgc tcggttgatc cgctcccgcg    3000
acattgtggc gacagccctg ggtcaactgg gccgagatcc gttgatcttc ctgcatccgc    3060
cagagggcgg gatgcgaaga atgcgatgcc gctcgccagt cgattggctg agctcatgag    3120
cggagaacga gatgacgttg gaggggcaag gtcgcgctga ttgctggggc aacacgtgga    3180
gcggatcggg gattgtcttt cttcagctcg ctgatgatat gctgacgctc aatgccgttt    3240
ggcctccgac taacgaaaat cccgcatttg gacggctgat ccgattggca cggcggacgg    3300
cgaatggcgg agcagacgct cgtccggggg caatgagata tgaaaaagcc tgaactcacc    3360
gcgacgtctg tcgagaagtt tctgatcgaa aagttcgaca gcgtctccga cctgatgcag    3420
ctctcggagg gcgaagaatc tcgtgctttc agcttcgatg taggagggcg tggatatgtc    3480
ctgcgggtaa atagctgcgc cgatggtttc tacaaagatc gttatgttta tcggcacttt    3540
gcatcggccg cgctcccgat tccggaagtg cttgacattg ggaatttcg acgtcatatg    3600 gatccgatga tctgctactt cacccctggaa cagggcgtgc tgacgggcaa gtacgcgccg    3660
```

-continued

```
ggcgccccgc ccccggccgg gtcccgggcc acggcaccca aaggtggccg ggccccgttg    3720
atgcggcgct ggctggacga cgacaaggtc ctcgggcgcg tcgagcggct cgtccgctc     3780 gccgaggagg ccgggctgac cacgcgcac  ctcgcgtggg tgctccagaa tcccgccgtc    3840
agcggggccg tcatcggctc gttcaacgcc gaacaggtcc tggccaacgc cgagtcggcc    3900
ggcgtccgtc tggagacgga cctgctggtg aggatcgacg aggtcctggg cgactccgtc    3960
gtgcacgacg aggagtagcc cccgggcggg gccggtggag gcggatgcga cgccgttcgt    4020
tccgggggct gccgtccgtt ccggttcggc gacggaggcg gatgcatccg cgcccgtccg    4080
gcccaccgcc cggcccgccc ggcatgccgg gcgcggggt  cgggcaccga ggtgcaagcg    4140
ccccgaccgt acgccgagcc gagccgaccc gtggcctctc ccgtccctcc tgaccgaccc    4200 tcccctccc  tcgtccttgc cgacaggttc gcccctactt ccgacgctcc cggagaggtc    4260
cactacggat gcgcattctg ttcaccacgt tccctggca  ctcccatcac ttccgatgg     4320 tcccactgga gcggcggcgc tggccgccgg gcatgaggtg cgggtcgcga gcgcgcccgc    4380
gctgatgccg gtcgtgaccg cgtccggcct gccggata   ccgtcggcc  aggacgtgga    4440 ccttgcctcc ctgtccaacg accgcagccg ggccgcctgg cacgttcagg accgctggcc    4500
cgacgactgg cccgtccgtc cggaactcct cgacgacgag cagttcgcgc tgatcgagaa    4560
cctgggacgg atgcagacgg tcatggcctc ggccatgctc gacgacctgc tgagcttcgc    4620
ccggtactgg cggcccgacc tggtggtgca cgacgccgtc agcctcgccg gcccggtggt    4680
cgccgccgcg ctgggcgtgc ccaacgtcag ccacctgtgg ggcactccgg gactccagcg    4740
catcgagctg cgccgcatgg gcggcgaacc gctgccggag tacgtccggc tgtacgagcg    4800
ggcgggaacg acgtgcgga  ccgagcccag tgcctggatc gaccccagtg cccccggcat    4860
ccggtacccg gccggaccga cctgccgtca gatgcggtac gtgccctaca acggcccggg    4920
cctgctgccg gactggctgc gccgggaacc gtcgggcagc cgggtctgcg tcacgtgggg    4980
cgccacctcc atggccctgc gcggcggcac cgtcgtcgaa ctcgtacgcc agtgcgtgga    5040
agccgccgcc gaggtggccg acgaggtcgt cgtcgcggtg accgaacaga ccgcgcgggc    5100
gctggaggac acgccgctgc cggaccacgc acgcgtcgcg gtcggattgc cgctgcacct    5160
gctggtgccg tcctgcgacc tcgtggtcca ccacggtggc gccggcacca gcatgaccgc    5220
cgcggtcgcg ggcgtacgac agctgctgat caccacccgg cccgagccca cggtcaacgg    5280
cacccggctg gccgcgtcgg gcgccgcccg gcacctgatg accacggagg tccccgccgc    5340
ccgggaggga gtgctgctgc tgcgcgccga gatggaccgt ctcctatcgg accccgcaca    5400
cggcgccgcc gcgcggcggc tggccgacgg catccgcacc cagcccgcac cggcgacgt    5460 ggtggcggag ctgacgcatc tcgtccggta ggtcgatccc gcccggaagg gatgaatctc    5520
gcccggcggg gacgactccc gcccgacagg aggagcaaga accatgcgcg ttctggtgac    5580
cacgtccccg tggcccaccc attacttcgt cgtccagccg ctggccgccg cgttccgcgc    5640
ggcgggccac gaagtcctcg tggcggccca gccgtccatg gcggacctgg tcacccggtc    5700
cggcctgccc atggccgccg tcggcagcga catcgacatg gtggacatcc gccgcaagac    5760
gctctcccag gaactggacg cccgtcagaa gccggggaa  cccgcccggg ccgacgacgg    5820
cggtcaggtc ttcgacacct ggcagcaggc caccctcgcc aacctcgacc cggtcatgga    5880
cctcgcccgg acctgaaaac cggacctggt gctcgccgac accatgtgcc cgccgggcct    5940
cgtcgccgca caggaactcg gcgtgccggg gatcc                              5975
```

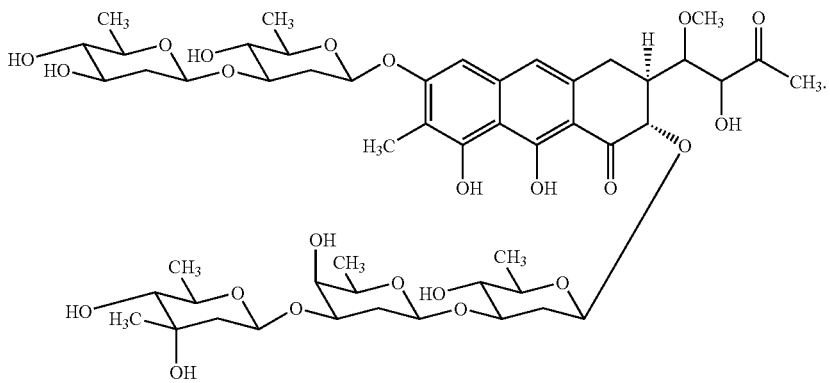

7. The compound of claim 1 having the following formula:
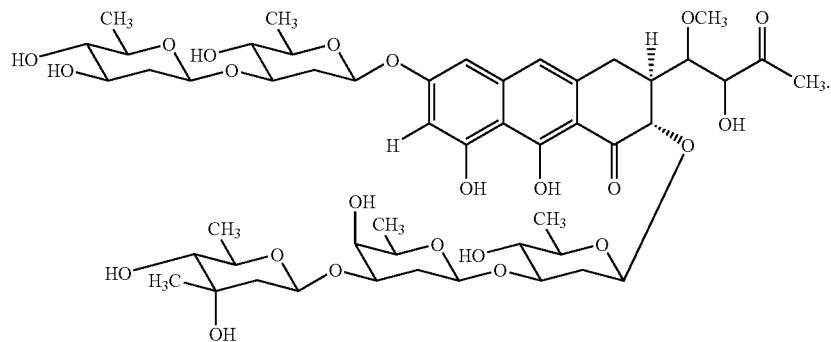
8. The compound of claim 1 having the following formula:
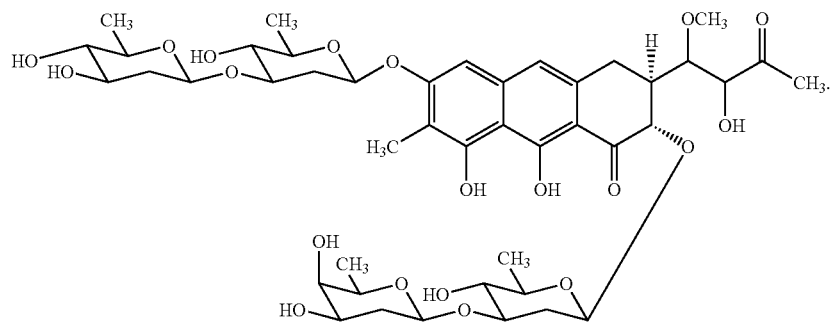
9. The compound of claim 1 having the following formula:
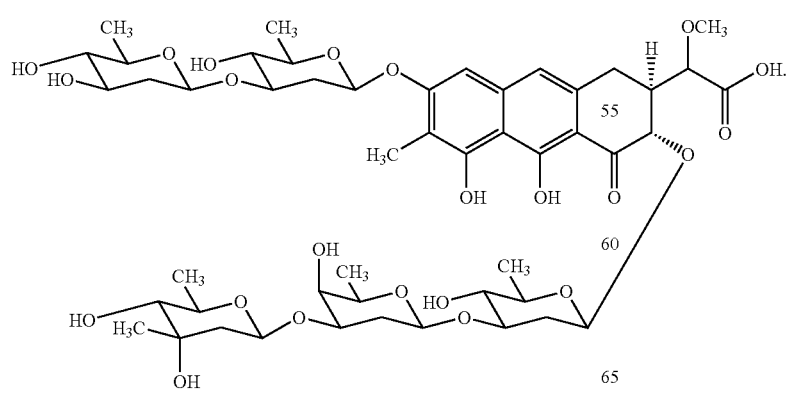

10. The compound of claim 1 having the following formula:
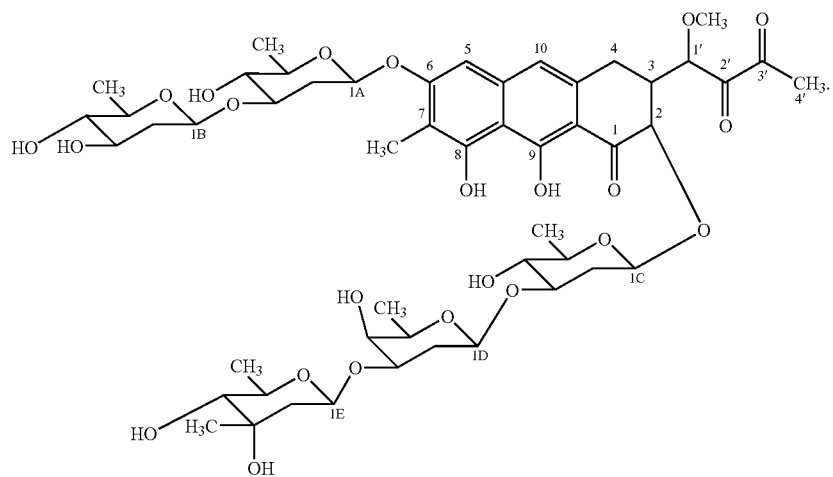

What is claimed is:

1. A compound having the following formula:

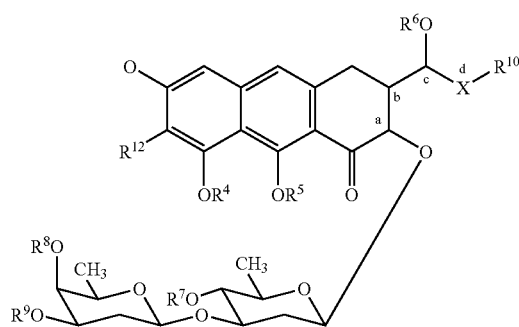

wherein
$R^1$, $R^2$, $R^3$, $R^4$, $R^5$, $R^6$, $R^7$ and $R^8$ are each, independently, hydrogen or a protecting group;
X is C=O or CH(OR$^{11}$), wherein $R^{11}$ is hydrogen or a protecting group;
$R^{10}$ is OH when X is C=O or C(O)CH$_3$ when X is CH(OR$^{11}$);
$R^9$ is hydrogen, a protecting group or

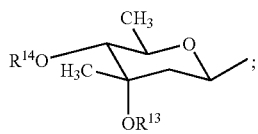

$R^{12}$ is methyl or hydrogen; and
the stereochemistry at carbons a, b and c is R, S or mixtures thereof:, and when X is CH(OR$^{11}$), the stereochemistry of d is R or S.

2. The compound of claim 1, wherein the protecting group comprises an alkyl group, a cycloalkyl group, a heterocyloalkyl group, a hydroxyalkyl group, a halogenated alkyl group, an alkoxyalkyl group, an alkenyl group, an alkynyl group, an aryl group, a heteroaryl group, an aralkyl group, an ester, a carbonate group, a carboxylic acid, an aldehyde, a keto group, an ether group, a urethane group, a silyl group, a sulfo-oxo group, or a combination thereof.

3. The compound of claim 1, wherein when $R^{11}$ is a protecting group, the protecting group is an alkyl group selected from the group consisting of methyl, ethyl, propyl, isopropyl, butyl, isobutyl and pentyl.

4. The compound of claim 1, wherein the stereochemistry at carbons a, b and c is S and the stereochemistry at d when X is CH(OH) is R.

5. The compound of claim 1, wherein $R^1$, $R^2$, $R^3$, $R^4$, $R^5$, $R^7$, $R^8$, $R^9$, $R^{11}$ are hydrogen; $R^{13}$ and $R^{14}$ are methyl; the stereochemistry at carbons a, b, and c is S; and the stereochemistry at d when X is CH(OH) is either R or S.

6. The compound of claim 1 having the following formula: